US011992324B2

(12) United States Patent
Lunner et al.

(10) Patent No.: US 11,992,324 B2
(45) Date of Patent: May 28, 2024

(54) SYSTEM FOR CAPTURING ELECTROOCULOGRAPHY SIGNALS

(71) Applicant: Oticon A/S, Smørum (DK)

(72) Inventors: Thomas Lunner, Smørum (DK); Martin Skoglund, Smørum (DK); Alejandro Lopez Valdes, Smørum (DK); Tanveer Bhuiyan, Smørum (DK)

(73) Assignee: Oticon A/S, Smørum (DK)

( * ) Notice: Subject to any disclaimer, the term of this patent is extended or adjusted under 35 U.S.C. 154(b) by 1574 days.

(21) Appl. No.: 16/014,763

(22) Filed: Jun. 21, 2018

(65) Prior Publication Data
US 2018/0368722 A1 Dec. 27, 2018

(30) Foreign Application Priority Data

Jun. 22, 2017 (EP) ..................... 17177544

(51) Int. Cl.
*A61B 5/398* (2021.01)
*A61B 3/113* (2006.01)
(Continued)

(52) U.S. Cl.
CPC .............. *A61B 5/398* (2021.01); *A61B 5/291* (2021.01); *A61B 5/6803* (2013.01);
(Continued)

(58) Field of Classification Search
None
See application file for complete search history.

(56) References Cited

U.S. PATENT DOCUMENTS

2007/0112277 A1 5/2007 Fischer et al.
2011/0170067 A1 7/2011 Sato et al.
(Continued)

FOREIGN PATENT DOCUMENTS

EP   3 185 590 A1   6/2017
EP   3 238 616 A1   11/2017
(Continued)

*Primary Examiner* — Kyle Zhai
(74) *Attorney, Agent, or Firm* — Birch, Stewart, Kolasch & Birch, LLP

(57) ABSTRACT

An electrooculography (EOG) signal capture system comprises a) a sensor array adapted for being located at one of a left or right ears of a user and/or for fully or partially being implanted in the head at left or right ears of a user, the sensor array comprising a number Ns of electric potential sensors, respectively, for sensing respective electric potentials from the user's head, where Ns is larger than or equal to two, b) electronic circuitry coupled to the sensor array and configured to provide at least two different beamformed signals ($S_{BF1}$, $S_{BF2}$), each being representative of a weighted combination of said electric potentials, or of signals derived therefrom, and wherein a difference between said at least two different beamformed signals ($\Delta P_{BF}=S_{BF1}-S_{BF2}$)—at least in a specific electrooculography mode of operation—represents an electrooculography signal ($\Delta P_{EOG}$) from one or both eyes of said user. A single-sensor EOG-system is further proposed. The invention may e.g. be used in hearing aids or other electronic wearables.

21 Claims, 10 Drawing Sheets

(51) Int. Cl.
*A61B 5/00* (2006.01)
*A61B 5/291* (2021.01)
*G06F 3/01* (2006.01)
*H04R 25/00* (2006.01)

(52) U.S. Cl.
CPC .......... *A61B 5/6817* (2013.01); *A61B 5/7207* (2013.01); *G06F 3/013* (2013.01); *H04R 25/40* (2013.01); *A61B 3/113* (2013.01); *A61B 5/0006* (2013.01)

(56) References Cited

U.S. PATENT DOCUMENTS

| | | |
|---|---|---|
| 2014/0198936 A1 | 7/2014 | Higgins et al. |
| 2014/0270290 A1* | 9/2014 | Cheung ................ H04R 25/405 381/316 |
| 2015/0238108 A1 | 8/2015 | Kanoh et al. |
| 2015/0289065 A1* | 10/2015 | Jensen ................ H04R 25/552 381/315 |
| 2016/0119726 A1 | 4/2016 | Pontoppidan et al. |
| 2016/0234610 A1* | 8/2016 | Jensen ................ H04R 25/552 |
| 2017/0035317 A1* | 2/2017 | Jung .................... A61B 3/0025 |
| 2018/0321739 A1* | 11/2018 | Park ................... G06F 3/04842 |

FOREIGN PATENT DOCUMENTS

| | | |
|---|---|---|
| EP | 3 477 964 A1 | 5/2019 |
| WO | WO 2019/036114 A1 | 2/2019 |

\* cited by examiner

SYSTEM FOR CAPTURING ELECTROOCULOGRAPHY SIGNALS

SUMMARY

The present application deals with a system for capturing electrooculography signals, e.g. in a hearing device, such as a hearing aid. In an embodiment, an estimation of eye-gaze angle (e.g. horizontal eye-gaze angle) of a user is provided based on the electrooculography signals. Functions of an electronic device, e.g. processing of a hearing aid, can e.g. be controlled fully or partially using electrooculography signals, e.g. an estimated eye gaze angle.

A Portable System for Capturing Electrooculography Signals:

In an aspect of the present application, a portable electrooculography (EOG) signal capture and/or eye gaze estimation system adapted for being worn by a user and using two or more electric potential sensors, e.g. comprising electrodes, to form a "beamformer" that 'looks' in the direction of an eye or both eyes of a user is provided. Potentially, an EOG (e.g. an earEOG) signal from one device only can thereby be provided. This has the advantage that EOG-potentials originating from the eye balls of the user can be processed in the device where they are captured (without having to be transferred to another device). Data from an eye gaze estimation system comprising sensors located at left and right ears of the user may be combined to provide a better estimate of an eye gaze angle of the user. Further, eye gaze information may be combined with other information, e.g. from one or more sensors, e.g. head orientation information (e.g. captured by acceleration and/or orientation sensors, e.g. embodied in a head tracker) to control functions of an electronic device, e.g. a hearing aid.

A portable electrooculography signal capture system (e.g. for eye gaze estimation) according to the present disclosure comprises

- a sensor array adapted for being located at one of a left or right ear of a user and/or for fully or partially being implanted in the head at a left or a right ear of a user, the sensor array comprising a number Ns of electric potential sensors, respectively, for sensing respective electric potentials from the user's head, where Ns is larger than or equal to two; and
- electronic circuitry coupled to the sensor array and configured to provide at least two different beamformed signals (SBF1, SBF2), each being representative of a weighted combination of said electric potentials, or of signals derived therefrom, and wherein a difference between said at least two different beamformed signals ($\Delta$PBF=SBF1−SBF2)—at least in a specific electrooculography (EOG) mode of operation—represents an electrooculography signal ($\Delta P_{EOG}$) from one or both eyes of said user.

Thereby an improved system for facilitating eye gaze estimation may be provided. In an embodiment, a measure of eye gaze from a sensor part located at a single one of a users' ears is configured to provide an estimate of a current eye gaze angle. This has the advantage of avoiding transmission of potentials from one ear to the other (or from both ears to an auxiliary device).

The term 'beamformed signal' is in the present context taken to mean, a signal that is a combination of a multitude of (input) signals, e.g. a weighted combination. The 'beamformed signal' Y may e.g. be implemented as a linear combination of a multitude of input signals $x_i$, i=1, . . . , M where M is the number of input signals (e.g. here electric potentials provided by electrodes or electric potential sensors): $Y=\Sigma_{i=1}^{M} w_i x_i$, and where $w_i$, i=1, . . . , M are generally complex weights. Other combinations may be used, cf. e.g. [Van Veen & Buckley; 1988] quoted below. The 'beamformed signal' may alternatively be termed the 'combined signal'.

In an embodiment, an electric potential sensor (EPS) comprises a sensing electrode configured to be coupled to the surface of the user's head (e.g. at or around an ear or in an ear canal), when the system (e.g. embodied in a hearing device) is operatively mounted on the user. In an embodiment, the sensing electrode is configured to be mounted in good electric contact with skin of the user. In an embodiment, the electric potential sensor (e.g. in the form of an EPIC) is configured to sense the electric field variations rather than sensing (small) electrical currents. This requires only one active electrode to create a readable voltage. Furthermore, direct skin contact is not necessary to sense the electric field. Different kinds of electric potential sensors are described in our co-pending European patent application 16205776.4 (published as EP3185590A1).

In an embodiment, the sensor array is configured to sense bioelectric signals due to eye movements, e.g. muscular contraction or changes of the electric eye-field potentials due to eye-bulb rotations, or eye gaze.

In general, the sensor array may comprise any number Ns of electric potential sensors, practically applicable in a given solution. The larger the number of sensors, the more specific the beamforming can be provided.

In an embodiment, the sensor part is configured to provide that the at least two electrical potential sensors are spatially spaced apart when the sensor part is operationally mounted at or in an ear (or in the head) of the user.

The electric circuitry may comprise at least two beamformers. In general, the at least two electric potential beamformers may have any convenient structure in the art, e.g. a generalized sidelobe canceller (GSC) structure. In an embodiment, the electric potential beamformers may comprise a minimum variance distortionless response (MVDR) beamformer, which (ideally) keeps the signals from a target direction (also referred to as a look direction) unchanged, while attenuating signals from (some) other directions maximally Beamformers for electric potential sensors (e.g. comprising individual electrodes) may be designed as is done in antenna array circuits (assuming the electrodes are the antenna elements).

In an embodiment, the portable electrooculography signal capture system comprises a reference potential for allowing said electric potentials to be referred to the same potential. In an embodiment, the eye gaze estimation system comprises a sensor, e.g. an electrode, for providing a reference potential, $P_{ref}$, from the user's body, e.g. the head.

In an embodiment, the portable electrooculography signal capture system comprises respective differential buffers to provide respective voltage difference signals from said electric potentials and said reference potential. In an embodiment, the eye gaze estimation system comprises a differential buffer for each electric potential $P_i$ providing an electric voltage difference signal $\Delta P_i = P_i - P_{ref}$. In an embodiment, the electric potentials $P_i$, i=1, . . . , Ns, are all referred to said reference potential $V_{ref}$, thereby providing voltage difference signal $\Delta P_i = P_i - P_{ref}$, i=1, . . . , Ns.

In an embodiment, the electronic circuitry is coupled to the sensor array via the differential buffers to thereby provide that the at least two different beamformed signals ($S_{BF1}$, $S_{BF2}$) are formed as a weighted combination of the voltage difference signals $\Delta P_i$, i=1, . . . , Ns. In an embodiment, the beamformed signals $S_{BFj}$ are linear combinations of the voltage difference signals $\Delta P_1$, e.g. $S_{BFj} = w_{j1} * \Delta P_1 + \ldots + w_{jNs} * \Delta P_{Ns}$, where the weights $w_{ji}$ are generally complex, frequency dependent values (e.g. fixed values for a fixed beamformer and time dependent values for an adaptive beamformer). In an embodiment, where Ns=2, $S_{BF1} = w_{11} * \Delta P_1 + w_{12} * \Delta P_2$, and $S_{BF2} = w_{21} * \Delta P_1 + w_{22} * \Delta P_2$.

In an embodiment, the beamformed signals ($S_{BF1}$, $S_{BF2}$) are formed by respective fixed beamformers. In an embodiment, the fixed beamformers are configured to have different target directions in the sense that they have maximum gain (or minimum attenuation) of signals from said target directions. In an embodiment, each fixed beamformer is configured to have minimum gain (or maximum attenuation) of signals from at least one of said target directions of the other fixed beamformers. In an embodiment, the eye gaze estimation system, e.g. the electric circuitry, comprises two fixed ($1^{st}$ and $2^{nd}$) beamformers having target directions towards front and rear parts of an eye of the user (front and rear being e.g. defined relative to a user's nose (defining a front direction)). In an embodiment, the electric circuitry is configured to provide that the two fixed ($1^{st}$ and $2^{nd}$) beamformers have target directions towards a left side of a left eye of the user and towards a right side of a right eye of the user, respectively, to thereby maximize the potential difference between the measured potentials of the eye liquid. In an embodiment, the electric circuitry is configured to provide that each of the two fixed ($1^{st}$ and $2^{nd}$) beamformers have minimum gain (or maximum attenuation) of signals from the target direction of the other fixed beamformer.

In an embodiment, the portable electrooculography signal capture system comprises a processor for executing an algorithm, or accessing stored data, providing corresponding values of eye gaze angle $\Delta\theta$ and said electrooculography signal ($\Delta P_{EOG}$). In an embodiment, the eye gaze estimation system comprises a processor for providing an estimate of eye gaze angle based on said electrooculography signal. In an embodiment, the algorithm or stored data is/are dependent on the implemented beamformers, e.g. different for beamformers directed to one eye and beamformers directed at left and right eyes. In an embodiment, the beamformers and/or the data providing $\Delta\theta(\Delta P_{EOG})$ are adapted to a particular user, e.g. a user's facial physiognomy.

In an embodiment, the electric circuitry is configured to provide that the two or more beamformers are adaptive and configured to maximize a difference between the beamformed signals.

In an embodiment, the electronic circuitry comprises a high pass filter for filtering said electrooculography signal and providing a high-pass filtered EOG signal, and a processor configured to estimate an eye gaze angle based on said high-pass filtered EOG signal. In an embodiment, the cut-off frequency for the high pass filter is below 100 Hz, e.g. below 20 Hz, such as below 10 Hz, or below 5 Hz.

In an embodiment, the captured electrooculography signals are used locally in a device, e.g. a hearing device, which comprise or is directly connected to the electrooculography signal capture system. In an embodiment, the captured electrooculography signals are transmitted to another device (e.g. a remote control device, a smartphone or similar communication device) for further processing, display, and/or use there. In an embodiment, the captured electrooculography signals are used for controlling functions of an electronic device, e.g. processing of a hearing aid. In an embodiment, a function of an electronic device is controlled fully or partially using an estimated eye gaze angle based on the captured electrooculography signals (or processed signals based thereon, e.g. an eye gaze angle).

In an aspect of the present application, a portable electrooculography (EOG) signal capture and/or eye gaze estimation system adapted for being worn by a user and using single electric potential sensor is provided by the present disclosure. The (single) electric potential sensor may be located in or at an ear of the user.

A portable electrooculography signal capture system (e.g. for eye gaze estimation) according to the present disclosure comprises a electric potential sensor adapted for being located at one of a left or right ear of a user and/or for fully or partially being implanted in the head at a left or a right ear of a user, the electric potential sensor being configured to sense electric potentials from the user's head and—at least in a specific electrooculography (EOG) mode of operation—to provide a voltage difference representing an electrooculography signal ($\Delta P_{EOG}$) from one or both eyes of said user.

Thereby an improved system for facilitating eye gaze estimation may be provided. In an embodiment, a measure of eye gaze from a sensor part located at a single one of a users' ears is configured to provide an estimate of a current eye gaze angle. This has the advantage of avoiding transmission of potentials from one ear to the other (or from both ears to an auxiliary device).

A Hearing Device:

In an aspect, the present disclosure further provides a hearing device e.g. a hearing aid, adapted for being located at or in an ear of a user and/or for being fully or partially implanted into the head of the user, and comprising a portable electrooculography signal capture system as described above, in the detailed description and in the claims.

In an embodiment, the hearing device comprises a forward audio signal path comprising an input unit for providing an electric input signal representative of sound, a configurable signal processor for executing a number of processing algorithms to provide a processed electric signal based on said electric input signal, and an output unit for providing stimuli perceivable as sound based on said processed signal, wherein said configurable signal processor is adapted to control one or more of said processing algorithms in dependence of the electrooculography signal, e.g. of an eye gaze angle estimated based on the captured electrooculography signals.

In an embodiment, the hearing device comprises an ITE part adapted for being located at or in an ear canal of the user wherein said ITE part comprises at least a part of said portable electrooculography signal capture system. In an embodiment, the hearing device comprises a BTE part adapted for being located at or behind an ear of the user wherein said BTE part comprises at least a part of said electrooculography signal capture system. In an embodiment, the hearing device comprises an implanted part adapted for being fully or partially implanted into the head of the user wherein said implanted part comprises at least a part of said electrooculography signal capture system.

In an embodiment, the hearing device additionally comprises one or more sensors for picking up potentials from the brain of the user, e.g. EEG potentials.

In an embodiment, the hearing device comprises a reference potential, e.g. a virtual ground, for use as reference for the electric (EOG) potentials and/or the potentials from the brain to provide electrooculography signals and/or brain wave or EEG signals. In an embodiment, different reference potentials are used for the EOG signals and the EEG signals.

In an embodiment, the configurable signal processor is adapted to control one or more of the processing algorithms in dependence of the electrooculography signal as well as the brain wave or EEG signals.

In an embodiment, the hearing device comprises a hearing aid, a headset, an earphone, an ear protection device or a combination thereof.

In an embodiment, the hearing device is adapted to provide a frequency dependent gain and/or a level dependent compression and/or a transposition (with or without frequency compression) of one or more frequency ranges to one or more other frequency ranges, e.g. to compensate for a hearing impairment of a user.

In an embodiment, the output unit comprises a number of electrodes of a cochlear implant or a vibrator of a bone conducting hearing device. In an embodiment, the output unit comprises an output transducer. In an embodiment, the output transducer comprises a receiver (loudspeaker) for providing the stimulus as an acoustic signal to the user. In an embodiment, the output transducer comprises a vibrator for providing the stimulus as mechanical vibration of a skull bone to the user (e.g. in a bone-attached or bone-anchored hearing device).

The hearing device comprises an input unit for providing an electric input signal representing sound. In an embodiment, the input unit comprises an input transducer, e.g. a microphone, for converting an input sound to an electric input signal. In an embodiment, the input unit comprises a wireless receiver for receiving a wireless signal comprising sound and for providing an electric input signal representing said sound.

In an embodiment, the hearing device comprises a directional microphone system adapted to spatially filter sounds from the environment, and thereby enhance a target acoustic source among a multitude of acoustic sources in the local environment of the user wearing the hearing device. In an embodiment, the directional system is adapted to detect (such as adaptively detect) from which direction a particular part of the microphone signal originates. This can be achieved in various different ways as e.g. described in the prior art. In hearing devices, a microphone array beamformer is often used for spatially attenuating background noise sources. Many beamformer variants can be found in literature, see, e.g., [Brandstein & Ward; 2001] and the references therein. The minimum variance distortionless response (MVDR) beamformer is widely used in microphone array signal processing. Ideally the MVDR beamformer keeps the signals from the target direction (also referred to as the look direction) unchanged, while attenuating sound signals from other directions maximally. The generalized sidelobe canceller (GSC) structure is an equivalent representation of the MVDR beamformer offering computational and numerical advantages over a direct implementation in its original form.

In an embodiment, the hearing device comprises an antenna and transceiver circuitry (e.g. a wireless receiver) for wirelessly receiving a direct electric input signal from another device, e.g. from an entertainment device (e.g. a TV-set), a communication device, a wireless microphone, or another hearing device. In an embodiment, the direct electric input signal represents or comprises an audio signal and/or a control signal and/or an information signal. In an embodiment, the hearing device comprises demodulation circuitry for demodulating the received direct electric input to provide the direct electric input signal representing an audio signal and/or a control signal e.g. for setting an operational parameter (e.g. volume) and/or a processing parameter of the hearing device. In general, a wireless link established by antenna and transceiver circuitry of the hearing device can be of any type. In an embodiment, the wireless link is established between two devices, e.g. between an entertainment device (e.g. a TV) and the hearing device, or between two hearing devices, e.g. via a third, intermediate device (e.g. a processing device, such as a remote control device, a smartphone, etc.). In an embodiment, the wireless link is used under power constraints, e.g. in that the hearing device is or comprises a portable (typically battery driven) device. In an embodiment, the wireless link is a link based on near-field communication, e.g. an inductive link based on an inductive coupling between antenna coils of transmitter and receiver parts. In another embodiment, the wireless link is based on far-field, electromagnetic radiation. Preferably, communication between the hearing device and the other device is based on some sort of modulation at frequencies above 100 kHz. Preferably, frequencies used to establish a communication link between the hearing device and the other device is below 70 GHz, e.g. located in a range from 50 MHz to 70 GHz, e.g. above 300 MHz, e.g. in an ISM range above 300 MHz, e.g. in the 900 MHz range or in the 2.4 GHz range or in the 5.8 GHz range or in the 60 GHz range (ISM=Industrial, Scientific and Medical, such standardized ranges being e.g. defined by the International Telecommunication Union, ITU). In an embodiment, the wireless link is based on a standardized or proprietary technology. In an embodiment, the wireless link is based on Bluetooth technology (e.g. Bluetooth Low-Energy technology). In an embodiment, the communication via the wireless link is arranged according to a specific modulation scheme, e.g. an analogue modulation scheme, such as FM (frequency modulation) or AM (amplitude modulation) or PM (phase modulation), or a digital modulation scheme, such as ASK (amplitude shift keying), e.g. On-Off keying, FSK (frequency shift keying), PSK (phase shift keying), e.g. MSK (minimum shift keying), or QAM (quadrature amplitude modulation), etc.

In an embodiment, the hearing device is a portable device, e.g. a device comprising a local energy source, e.g. a battery, e.g. a rechargeable battery.

The hearing device comprises a forward or signal path between an input unit (e.g. an input transducer, such as a microphone or a microphone system and/or direct electric input (e.g. a wireless receiver)) and an output unit, e.g. an output transducer. The signal processor is located in the forward path. In an embodiment, the signal processor is adapted to provide a frequency dependent gain according to a user's particular needs. In an embodiment, the hearing device comprises an analysis path comprising functional components for analyzing the input signal (e.g. determining a level, a modulation, a type of signal, an acoustic feedback estimate, etc.). In an embodiment, some or all signal processing of the analysis path and/or the signal path is conducted in the frequency domain. In an embodiment, some or all signal processing of the analysis path and/or the signal path is conducted in the time domain.

In an embodiment, the hearing devices comprise an analogue-to-digital (AD) converter to digitize an analogue input (e.g. from an input transducer, such as a microphone, or from a sensor, e.g. an electric potential sensor) with a predefined sampling rate adapted to the expected time-variation of the signal in question to be sampled, e.g. 20 kHz for an audio signal or 1 kHz for an EOG signal. In an embodiment, the hearing devices comprise a digital-to-analogue (DA) converter to convert a digital signal to an analogue output signal, e.g. for presenting an electric signal representing audio to a user via an output transducer.

In an embodiment, the hearing device, e.g. the microphone unit, and or the transceiver unit comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the (time-)frequency domain.

In an embodiment, the hearing device comprises a number of detectors configured to provide status signals relating to a current physical environment of the hearing device (e.g. the current acoustic environment), and/or to a current state of the user wearing the hearing device, and/or to a current state or mode of operation of the hearing device. Alternatively or additionally, one or more detectors may form part of an external device in communication (e.g. wirelessly) with the hearing device. An external device may e.g. comprise another hearing device, a remote control, and audio delivery device, a telephone (e.g. a Smartphone), an external sensor, etc.

In an embodiment, one or more of the number of detectors operate(s) on the full band signal (time domain). In an embodiment, one or more of the number of detectors operate(s) on band split signals ((time-) frequency domain), e.g. in a limited number of frequency bands.

In an embodiment, the number of detectors comprises a level detector for estimating a current level of a signal of the forward path. In an embodiment, the predefined criterion comprises whether the current level of a signal of the forward path is above or below a given (L-)threshold value. In an embodiment, the level detector operates on the full band signal (time domain) In an embodiment, the level detector operates on band split signals ((time-) frequency domain).

In a particular embodiment, the hearing device comprises a voice detector (VD) for estimating whether or not (or with what probability) an input signal comprises a voice signal (at a given point in time). A voice signal is in the present context taken to include a speech signal from a human being. It may also include other forms of utterances generated by the human speech system (e.g. singing). In an embodiment, the voice detector unit is adapted to classify a current acoustic environment of the user as a VOICE or NO-VOICE environment. This has the advantage that time segments of the electric microphone signal comprising human utterances (e.g. speech) in the user's environment can be identified, and thus separated from time segments only (or mainly) comprising other sound sources (e.g. artificially generated noise). In an embodiment, the voice detector is adapted to detect as a VOICE also the user's own voice. Alternatively, the voice detector is adapted to exclude a user's own voice from the detection of a VOICE.

In an embodiment, the number of detectors comprises a movement detector, e.g. an acceleration sensor. In an embodiment, the movement detector is configured to detect movement of the user's facial muscles and/or bones, e.g. due to speech or chewing (e.g. jaw movement) and to provide a detector signal indicative thereof.

In an embodiment, the hearing device comprises a classification unit configured to classify the current situation based on input signals from (at least some of) the detectors, and possibly other inputs as well. In the present context 'a current situation' is taken to be defined by one or more of
a) the physical environment (e.g. including the current electromagnetic environment, e.g. the occurrence of electromagnetic signals (e.g. comprising audio and/or control signals) intended or not intended for reception by the hearing device, or other properties of the current environment than acoustic);
b) the current acoustic situation (input level, feedback, etc.), and
c) the current mode or state of the user (movement, temperature, cognitive load, etc.);
d) the current mode or state of the hearing device (program selected, time elapsed since last user interaction, etc.) and/or of another device in communication with the hearing device.

In an embodiment, the configurable signal processor is adapted to control one or more of the processing algorithms in dependence of the electrooculography signal as well as the status signals from one or more of the detectors.

In an embodiment, the hearing device comprises an acoustic (and/or mechanical) feedback suppression system. In an embodiment, the hearing device further comprises other relevant functionality for the application in question, e.g. compression, noise reduction, etc.

Use:

In an aspect, use of a portable electrooculography signal capture system as described above, in the 'detailed description of embodiments' and in the claims, is moreover provided. In an embodiment, use is provided in a system comprising audio distribution. In an embodiment, use is provided in a system comprising one or more hearing aids (e.g. hearing instruments), headsets, ear phones, active ear protection systems, etc., e.g. in handsfree telephone systems, teleconferencing systems, public address systems, karaoke systems, classroom amplification systems, etc.

A Method:

In an aspect, a method of capturing an electrooculography signal from a user is furthermore provided by the present application. The method comprises a) providing a number Ns of electrical potentials from respective electric potential sensors located on or in one side of the user's head, where Ns is larger than or equal to two. The method further comprises b) providing at least two different beamformed signals (SBF1, SBF2), each being representative of a weighted combination of said electric potentials, or of signals derived therefrom, and wherein a difference between said at least two different beamformed signals ($\Delta P_{BF} = S_{BF1} - S_{BF2}$)—at least in a specific electrooculography mode of operation—represents an electrooculography signal ($\Delta P_{EOG}$) from one or both eyes of said user.

In an embodiment, the method comprises a prior calibration step for calibrating an estimation of eye gaze angle from said difference between said at least two different beamformed signals.

In an embodiment, the method comprises estimating an eye gaze angle from the captured electrooculography signals.

In an embodiment, the method comprises controlling a function of an electronic device, e.g. a hearing aid, based on the captured electrooculography signals.

It is intended that some or all of the structural features of the portable electrooculography signal capture system described above, in the 'detailed description of embodiments' or in the claims can be combined with embodiments of the method, when appropriately substituted by a corresponding process and vice versa. Embodiments of the method have the same advantages as the corresponding systems.

A Computer Readable Medium:

In an aspect, a tangible computer-readable medium storing a computer program comprising program code means for causing a data processing system to perform at least some (such as a majority or all) of the steps of the method described above, in the 'detailed description of embodiments' and in the claims, when said computer program is executed on the data processing system is furthermore provided by the present application.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

A Computer Program:

A computer program (product) comprising instructions which, when the program is executed by a computer, cause the computer to carry out (steps of) the method described above, in the 'detailed description of embodiments' and in the claims is furthermore provided by the present application.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

A Hearing System:

In a further aspect, a hearing system comprising left and right hearing devices, e.g. left and right hearing aids, adapted for being located at or in left and right ears of a user, and comprising an electrooculography signal capture system as described above, in the 'detailed description of embodiments', and in the claims is furthermore provided.

In a further aspect, a hearing system comprising left and right hearing devices, e.g. left and right hearing aids as described above, in the 'detailed description of embodiments', and in the claims is furthermore provided.

In an embodiment, the hearing system comprises an auxiliary device, e.g. a remote control, a smartphone, or other portable or wearable electronic device, such as a smartwatch or the like.

In an embodiment, the hearing system is adapted to establish a communication link between the left and right hearing devices and/or an auxiliary device to provide that information (e.g. control and status signals, signals related to electric potentials from the body of the user, e.g. EEG and/or EOG signals, and possibly audio signals) can be exchanged or forwarded from one to the other.

In an embodiment, the auxiliary device is or comprises a remote control for controlling functionality and operation of the hearing device(s). In an embodiment, the function of a remote control is implemented in a SmartPhone, the SmartPhone possibly running an APP allowing to control the functionality of the audio processing device via the SmartPhone (the hearing device(s) comprising an appropriate wireless interface to the SmartPhone, e.g. based on Bluetooth or some other standardized or proprietary scheme).

An APP:

In a further aspect, a non-transitory application, termed an APP, is furthermore provided by the present disclosure. The APP comprises executable instructions configured to be executed on an auxiliary device to implement a user interface for a portable electrooculography signal capture system, a hearing device or a hearing system described above in the 'detailed description of embodiments', and in the claims. In an embodiment, the APP is configured to run on cellular phone, e.g. a smartphone, or on another portable device allowing communication with said hearing device or said hearing system.

Definitions:

In the present context, a 'hearing device' refers to a device, such as a hearing aid, e.g. a hearing instrument, or an active ear-protection device, or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing device may be configured to be worn in any known way, e.g. as a unit arranged behind the ear with a tube leading radiated acoustic signals into the ear canal or with an output transducer, e.g. a loudspeaker, arranged close to or in the ear canal, as a unit entirely or partly arranged in the pinna and/or in the ear canal, as a unit, e.g. a vibrator, attached to a fixture implanted into the skull bone, as an attachable, or entirely or partly implanted, unit, etc. The hearing device may comprise a single unit or several units communicating electronically with each other. The loudspeaker may be arranged in a housing together with other components of the hearing device, or may be an external unit in itself (possibly in combination with a flexible guiding element, e.g. a dome-like element).

More generally, a hearing device comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit (e.g. a signal processor, e.g. comprising a configurable (programmable) processor, e.g. a digital signal processor) for processing the input audio signal and an output unit for providing an audible signal to the user in dependence on the processed audio signal. The signal processor may be adapted to process the input signal in the time domain or in a number of frequency bands. In some hearing devices, an amplifier and/or compressor may constitute the signal processing circuit. The signal processing circuit typically comprises one or more (integrated or separate) memory elements for executing programs and/or for storing parameters used (or potentially used) in the processing and/or for storing information relevant for the function of the hearing device and/or for storing information (e.g. processed information, e.g. provided by the signal processing circuit), e.g. for use in connection with an interface to a user and/or an interface to a programming device. In some hearing devices, the output unit may comprise an output transducer, such as e.g. a loudspeaker for providing an air-borne acoustic signal or a vibrator for providing a structure-borne or liquid-borne acoustic signal. In some hearing devices, the output unit may comprise one or more output electrodes for providing electric signals (e.g. a multi-electrode array for electrically stimulating the cochlear nerve).

In some hearing devices, the vibrator may be adapted to provide a structure-borne acoustic signal transcutaneously or percutaneously to the skull bone. In some hearing devices, the vibrator may be implanted in the middle ear and/or in the inner ear. In some hearing devices, the vibrator may be adapted to provide a structure-borne acoustic signal to a middle-ear bone and/or to the cochlea. In some hearing devices, the vibrator may be adapted to provide a liquid-borne acoustic signal to the cochlear liquid, e.g. through the oval window. In some hearing devices, the output electrodes may be implanted in the cochlea or on the inside of the skull bone and may be adapted to provide the electric signals to the hair cells of the cochlea, to one or more hearing nerves, to the auditory brainstem, to the auditory midbrain, to the auditory cortex and/or to other parts of the cerebral cortex.

A hearing device, e.g. a hearing aid, may be adapted to a particular user's needs, e.g. a hearing impairment. A configurable signal processing circuit of the hearing device may be adapted to apply a frequency and level dependent compressive amplification of an input signal. A customized frequency and level dependent gain (amplification or compression) may be determined in a fitting process by a fitting system based on a user's hearing data, e.g. an audiogram, using a fitting rationale (e.g. adapted to speech). The frequency and level dependent gain may e.g. be embodied in processing parameters, e.g. uploaded to the hearing device via an interface to a programming device (fitting system), and used by a processing algorithm executed by the configurable signal processing circuit of the hearing device.

A 'hearing system' refers to a system comprising one or two hearing devices, and a 'binaural hearing system' refers to a system comprising two hearing devices and being adapted to cooperatively provide audible signals to both of the user's ears. Hearing systems or binaural hearing systems may further comprise one or more 'auxiliary devices', which communicate with the hearing device(s) and affect and/or benefit from the function of the hearing device(s). Auxiliary devices may be e.g. remote controls, audio gateway devices, mobile phones (e.g. SmartPhones), or music players. Hearing devices, hearing systems or binaural hearing systems may e.g. be used for compensating for a hearing-impaired person's loss of hearing capability, augmenting or protecting a normal-hearing person's hearing capability and/or conveying electronic audio signals to a person. Hearing devices or hearing systems may e.g. form part of or interact with public-address systems, active ear protection systems, handsfree telephone systems, car audio systems, entertainment (e.g. karaoke) systems, teleconferencing systems, classroom amplification systems, etc.

Embodiments of the disclosure may e.g. be useful in applications such as hearing aids or other electronic wearables.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

The figures are schematic and simplified for clarity, and they just show details which are essential to the understanding of the disclosure, while other details are left out. Throughout, the same reference signs are used for identical or corresponding parts.

Figure 1A:
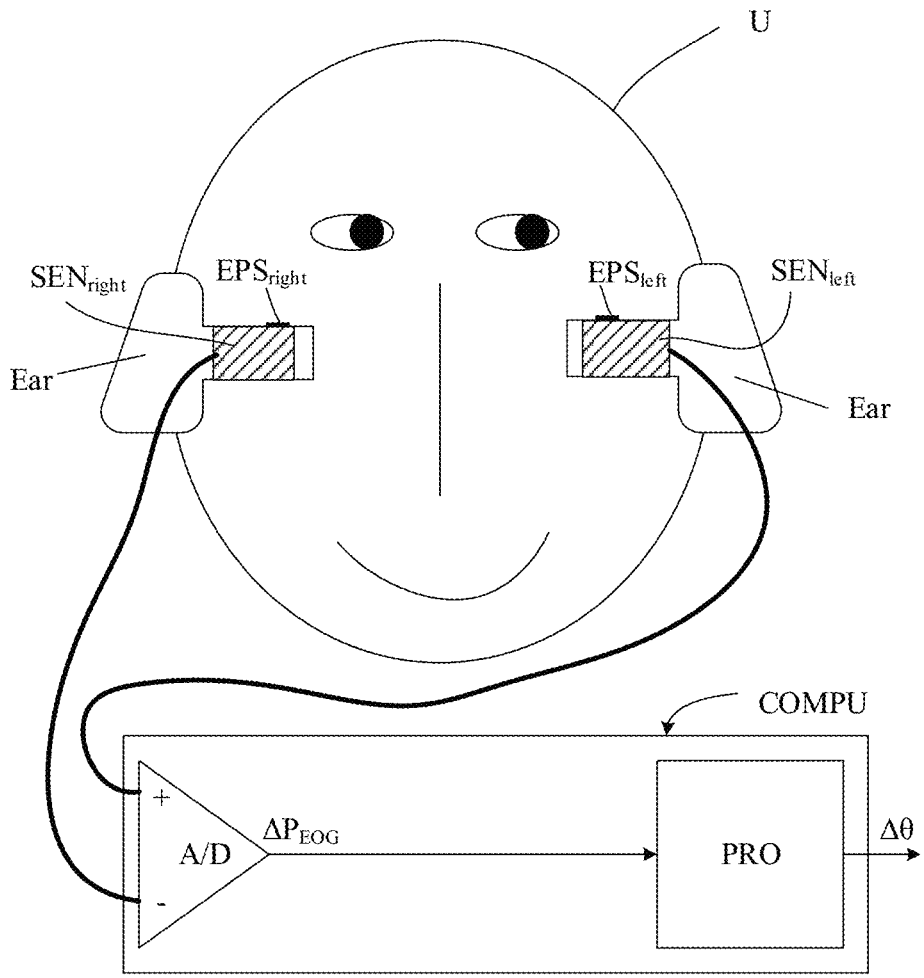
FIG. 1A schematically shows a configuration of an eye gaze estimation system according to the prior art.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

In an aspect of the present application, a electrooculography signal capturing system, e.g. an eye gaze estimation system, is provided. The system comprises a sensor part adapted for being located at or in a left or a right ear and/or for fully or partially being implanted in the head at a left or a right ear of a user. The sensor part comprises at least two electrical potential sensors for sensing respective electrical potentials ($P_1$, $P_2$) from the user's head. The e system further comprises electronic circuitry coupled to the sensor array and configured to provide at least two different beamformed signals ($S_{BF1}$, $S_{BF2}$), each being representative of a weighted combination of said electric potentials, or of signals derived therefrom, and wherein a difference between said at least two different beamformed signals ($\Delta P_{BF}=S_{BF1}=S_{BF2}$)—at least in a specific electrooculography mode of operation—represents an electrooculography signal ($\Delta P_{EOG}$) from one or both eyes of said user. The electronic circuitry may further comprise a processor for providing an estimate of a current eye gaze angle in dependence of said EOG signal ($\Delta P_{EOG}$) or a processed version thereof.

An aspect of the present application also relates to the field of hearing devices, e.g. hearing aids.

In the following, some signal names may alternatingly comprise subscripts $X_y$, or be written in normal form (Xy, without subscripts) without any intended difference in meaning, e.g. an electrooculography signal may intermittently be denoted $\Delta P_{EOG}$ or $\Delta PEOG$, etc.

FIG. 1A shows a configuration of an eye gaze estimation system according to the prior art, cf. e.g. our co-pending European patent application 16205776.4 (published as EP3185590A1). The eye gaze estimation system of FIG. 1A is worn by a user U, and comprises left and right sensor parts ($SEN_{left}$, $SEN_{right}$) adapted for being located at or in left and right ears (Ear) and/or for fully or partially being implanted in the head at left and right ears of a user. The left and right sensor parts comprises a left and a right electrical potential sensor ($EPS_{left}$, $EPS_{right}$), respectively, for sensing respective electrical potentials ($P_{left}$, $P_{right}$) from the user's head. The eye gaze estimation system further comprises electronic circuitry (COMPU) electrically coupled to the respective left and right electrical potential sensor parts ($SEN_{left}$, $SEN_{right}$) and configured to determine a single channel amplified output ($\Delta P$) representative of a difference between said left and right electrical potentials. The single channel amplified output ($\Delta P$) represents—at least in a specific electro-oculography (EOG) mode of operation—an EOG signal ($\Delta P_{EOG}$). In the embodiment of FIG. 1A, the electric circuitry comprises an analogue to digital converter A/D for providing an amplified, digitized version of the difference between the right and left electric potentials ($P_{left}$, $P_{right}$) provided by the respective left and right electrical potential sensors ($EPS_{left}$, $EPS_{right}$). The electronic circuitry (COMPU) further comprises a signal processor (PRO) configured to estimate an eye gaze angle ($\Delta\theta$) based on the (possibly further processed, e.g. filtered) EOG signal ($\Delta P_{EOG}$).

Figure 1B:
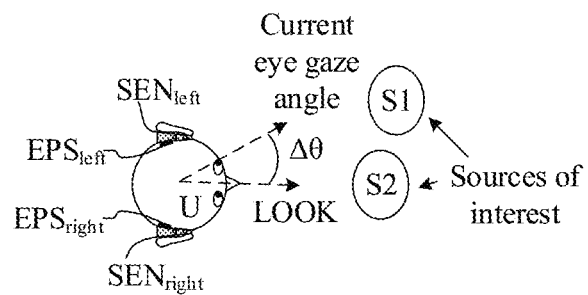
FIG. 1B shows a definition of eye gaze angle relative to a look direction of a user in the scenario of FIG. 1A, FIG. 2A schematically shows a configuration of an eye gaze estimation system according to a first embodiment of the present disclosure.

FIG. 1B illustrates a definition of a (horizontal) eye gaze angle $\Delta\theta$ relative to a look direction (LOOK) of a user (U) in the setup of FIG. 1A. The user wears an electrooculography signal capturing system, e.g. eye gaze estimation system, according to the present disclosure (illustrated by left and right electrical potential sensor parts ($SEN_{left}$, $SEN_{right}$) located at the ears of the user (U), e.g. embodied in left and right hearing devices, e.g. hearing aids. The look direction (LOOK) is e.g. defined by the nose of the user (and/or the microphone axes of the hearing devices when mounted at the ears of the user), and the eye gaze angle $\Delta\theta$ is simply an angle in a horizontal plane defining a current gaze direction of the eyes of the user relative to the look direction, e.g. as defined by the location of the pupils in the eye balls of the user (i.e. if the user 'looks' in the look direction, the eye gaze angle is 0°). Two (e.g. acoustic) Sources of interest S1, S2 are illustrated, and in the illustrated scenario, the eye gaze of the user can be assumed to be limited to the locations of those two sources of interest.

Figure 2A:
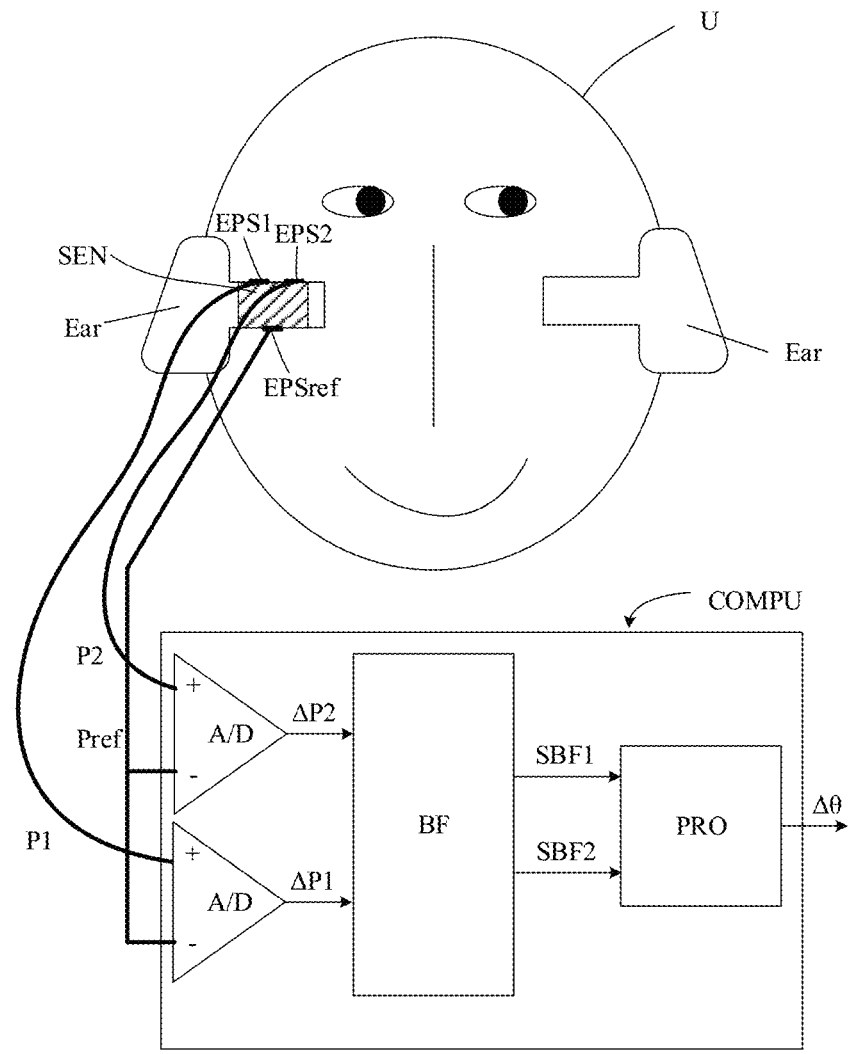
FIG. 2B shows a definition of eye gaze angle relative to a look direction of a user in the scenario of FIG. 2A.

FIG. 2A shows a configuration of an eye gaze estimation system according to a first embodiment of the present disclosure. The system is similar to the system of FIG. 1A but differs in that a monaural estimation of eye gaze angle is provided (only one location of the sensor array is necessary, here at the right ear (Ear) of the user (U)). A user (U) wears an ear piece comprising first and second electric potential sensors (EPS1, EPS2), e.g. electrodes, for ping up first and second electric potentials from the user's head, and a reference sensor (EPSref), e.g. an electrode, for picking up a reference potential from the user's body. The ear piece may form part of a hearing device, or be a mere carrier of an eye gaze estimation system according to the present disclosure. The ear piece is located in an ear canal of the user, to ensure a proper contact between the electrodes and the skin/tissue of the ear canal. The eye gaze estimation system further comprises electronic circuitry (COMPU) coupled to the sensor array (EPS1, EPS2, EPSref) and configured to provide an estimate of a current eye gaze angle $\Delta\theta$ of the user.

Figure 4:
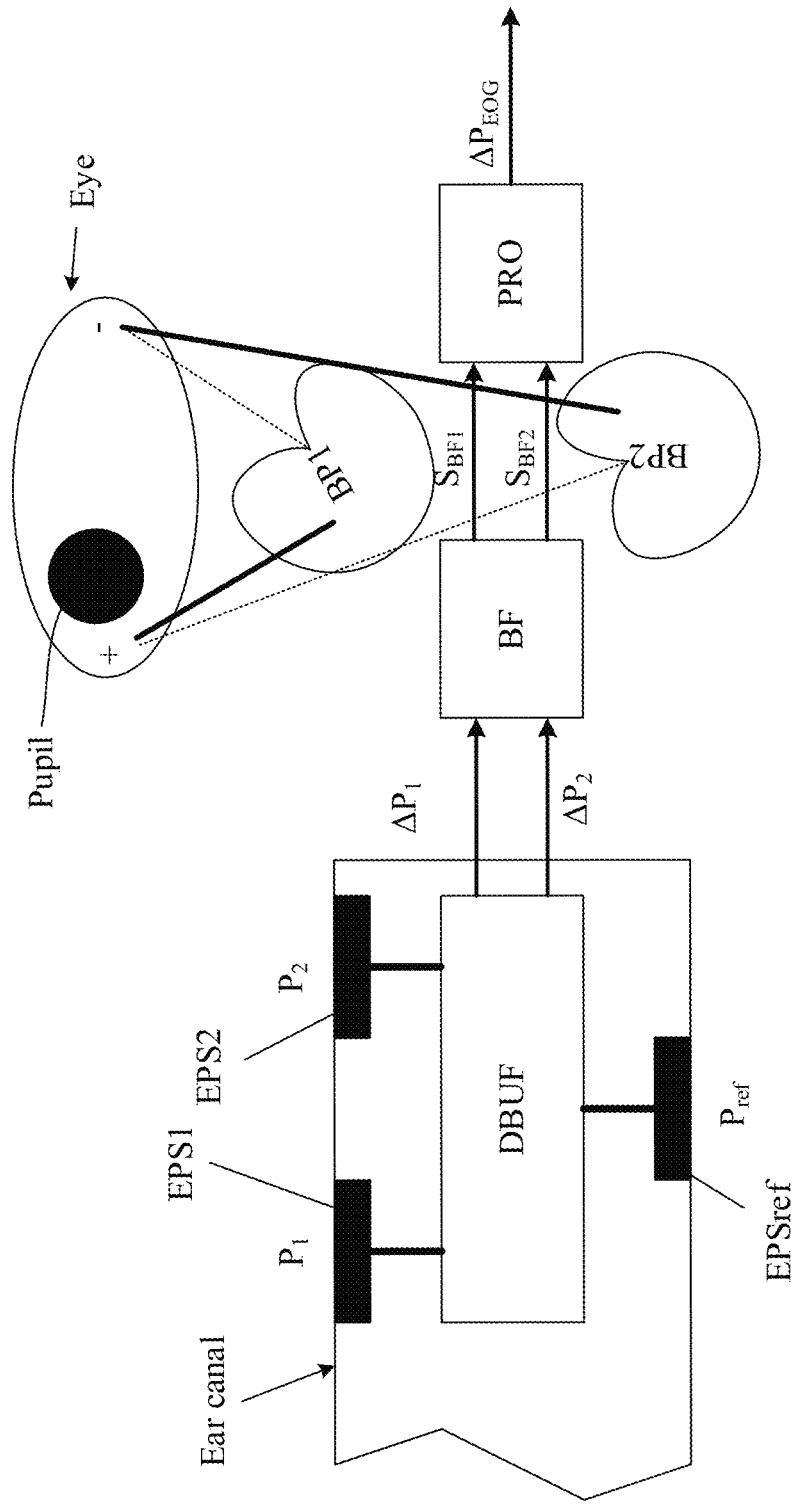

The electronic circuitry (COMPU) comprises respective differential buffers (here analogue to digital converters, A/D) to provide respective voltage difference signals (ΔP1, ΔP2) from the electric potentials (P1, P2) and the reference potential Pref. The electronic circuitry (COMPU) further comprises an electric potential beamformer (BF) providing two different beamformed signals (SBF1, SBF2), each being formed as a weighted combination of the electric potentials (P1, P2), or of signals derived therefrom (e.g. voltage difference signals (ΔP1, ΔP2)). The beamformed signals are e.g. formed by respective fixed beamformers (e.g. as illustrated in FIG. 4). The electronic circuitry (COMPU) further comprises a processor for executing an algorithm, or accessing stored data, providing corresponding values of eye gaze angle Δθ and electrooculography signal ($\Delta P_{EOG}$), cf. e.g. FIG. 5, where the electrooculography signal ($\Delta P_{EOG}$) is provided as a combination of the beamformed signals (SBF1, SBF2), e.g. as a difference between the beamformed signals ($\Delta PEOG=SBF1-SBF2$).

The electronic circuitry (COMPU) or parts thereof (e.g. the beamformer (BF) and/or the processor (PR)) may be located in the ear piece, or be located in another device, e.g. form part of a hearing device (e.g. located behind an ear of the user) or another electronic device adapted for processing the electrooculography signals. Preferably, at least the differential buffers (A/D) are located in the ear piece. Thereby the electric connections to the sensor array (e.g. the electrodes) can be wired. The voltage difference signals (ΔP1, ΔP2) may e.g. be wirelessly transmitted to another device, e.g. another part (e.g. a behind the ear (BTE) part) of a hearing device, and further processed there.

Functionality (e.g. beamforming of a microphone system) of an electronic device, e.g. a hearing device, comprising the earpiece or in communication with the ear piece, may be controlled via an estimate of a current eye gaze.

Figure 2B:
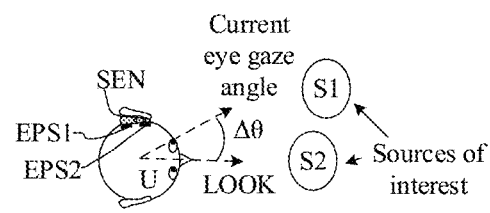

FIG. 2B shows a definition of eye gaze angle Δθ relative to a look direction (LOOK) of a user (U) in the scenario of FIG. 2A (only the ear piece/sensor array SEN is located at the right ear in FIG. 2A and in the left ear in FIG. 2B; ideally, FIG. 2A and FIG. 2B should correspond). FIG. 2B is similar to FIG. 1B, apart from the fact that only one sensor array (SEN) is present in the scenario of FIG. 2B.

Figure 3:
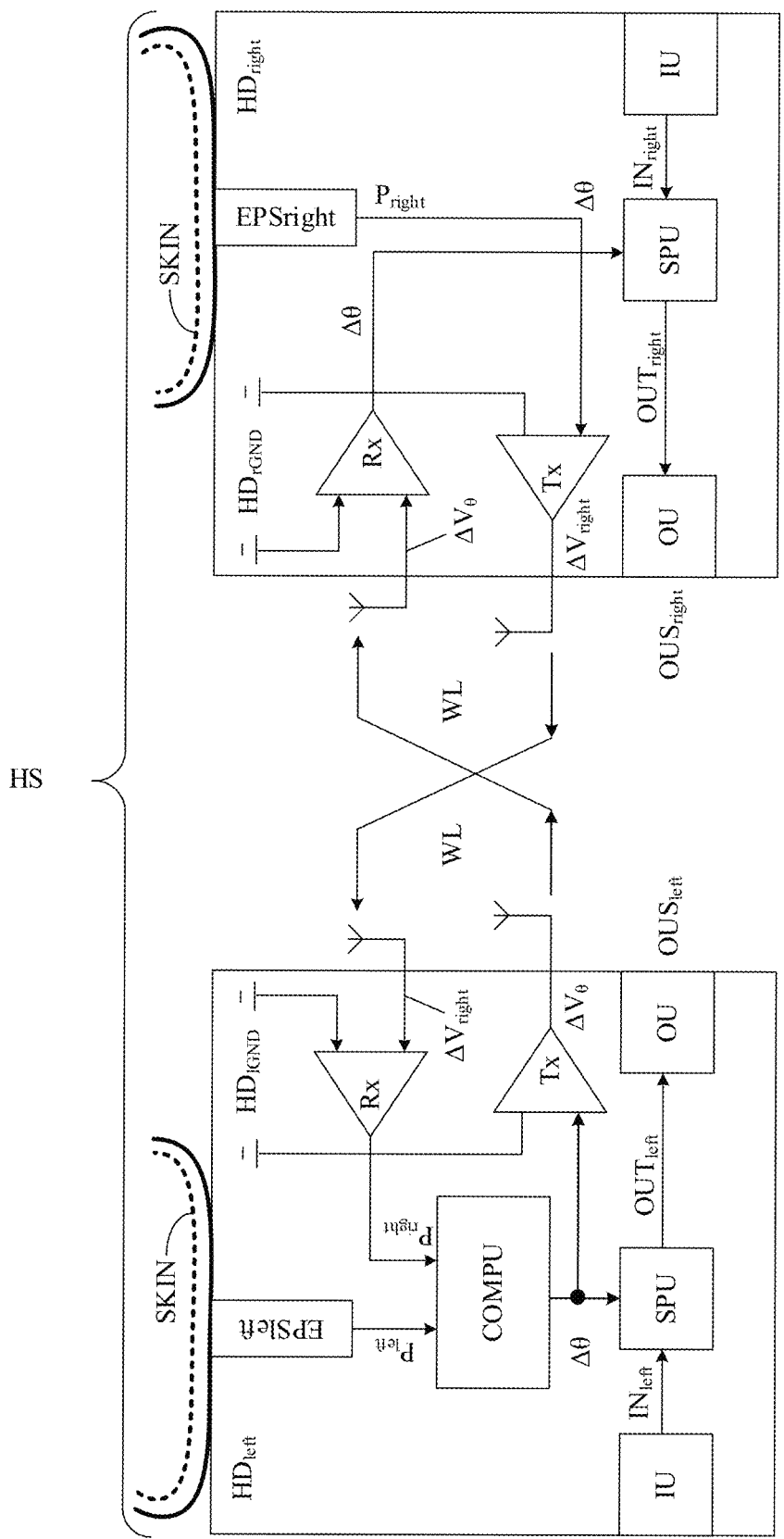
FIG. 3 shows a binaural hearing system comprising left and right hearing devices adapted for exchanging data between them via a wireless link and an eye gaze angle detection system according to an embodiment of the present disclosure, FIG. 4 schematically illustrates the capture of electrooculography signals from a user's eye using beamforming according to the present disclosure.

FIG. 3 shows a binaural hearing system comprising left and right hearing devices adapted for exchanging data between them via a wireless link and an eye gaze angle detection system according to an embodiment of the present disclosure.

FIG. 3 shows an embodiment of a hearing system (HS) comprising left and right hearing devices ($HD_{left}$, $HD_{right}$) adapted for being mounted at or in an ear of a user. The hearing system comprises an eye gaze estimation system according to the present disclosure. The left and right hearing devices each comprises a number of electric potential sensor ($EPS_{left}$, $EPS_{right}$) (one is shown but it might be two or more as illustrated in FIG. 2A) located at or accessible from a surface of a housing of the hearing devices to allow electrodes of the respective electric potential sensors to contact the skin (SKIN) of the user when the hearing devices are operationally mounted at the respective ears of the user. The electric potential sensors ($EPS_{left}$, $EPS_{right}$) are adapted to pick up a low-voltage electric potential from the user's body ($P_{left}$, $P_{right}$). The potential $P_{right}$ picked up at the right ear is transferred to the left ear, e.g. via a wired connection (cf. e.g. FIG. 1A) or as shown in FIG. 3 via a wireless link. The determination of voltage difference signals $\Delta P_{EOG}$ is performed in an amplifier and processing unit (COMPU), here shown to be located in the left hearing device ($HD_{left}$).

Each of the left and right hearing devices ($HD_{left}$, $HD_{right}$) comprises a forward path for propagating a signal representing sound from an input unit (IU) to an output unit (OU). The hearing devices each comprises an input unit (IU) for providing an electric input signal ($IN_{left}$, $IN_{right}$) based on an input sound signal. The input unit (IU) may comprise an input transducer, e.g. a microphone or an accelerometer or other vibration sensor. The hearing device (e.g. the forward path) comprises a signal processor (SPU), e.g. adapted to provide a frequency dependent gain to compensate for a hearing loss of a user, and/or to otherwise enhance the electric input signal ($IN_{left}$, $IN_{right}$) and to provide a processed electric signal ($OUT_{left}$, $OUT_{right}$). The hearing devices further comprise an output unit (OU) for providing a stimulus ($OUS_{left}$, $OUS_{right}$) perceived by the user as an acoustic signal based on the processed electric signal. In an embodiment, an output unit comprises a number of electrodes of a cochlear implant or a vibrator of a bone conducting hearing device. In an embodiment, an output unit comprises a receiver (speaker) for providing the stimulus as an acoustic signal to the user.

The (configurable) signal processor (SPU) is configured to process the electric input signal ($IN_{left}$, $IN_{right}$) depending on a number of processing algorithms and to provide a resulting processed signal ($OUT_{left}$, $OUT_{right}$). One or more of the signal processing algorithms are parameterized and parameters controllable in dependence on detectors or analysis of properties of the present environment of the user and/or of the present condition of the user. For example, the processing performed by the signal processor (SPU) may be influenced by the resulting EOG, and/or EEG measurements (e.g. based on voltage difference signal $\Delta V_{EOG}$ or $\Delta V_{EEG}$ or data derived therefrom, possibly combined with other parameters). This is illustrated in FIG. 3 by control signal Δθ from the amplifier and processing unit (COMPU) to the signal processor (SPU).

The hearing system (HS) is configured to establish a wireless link between the left and right hearing devices (at least for the transfer of potential(s) picked up by the electric potential sensor(s) $EPS_{right}$ of the right hearing device ($HD_{right}$) to the left hearing device ($HD_{left}$) and for transferring a resulting estimate of eye gaze angle Δθ from the amplifier and processing unit (COMPU) of the left hearing device ($HD_{left}$) to the right hearing device ($HD_{right}$). The wireless link comprises antenna and transceiver circuitry in the left and right hearing devices ($HD_{left}$, $HD_{right}$) allowing the transmission of a signal representing a voltage difference between the hearing devices. To that end, each of the left and right hearing devices ($HD_{left}$, $HD_{right}$) are configured to provide respective ground potentials $P(HD_{lGND})$, and $P(HD_{rGND})$, which are used as reference for voltages $P_{left}$, $P_{right}$ provided by electric potential sensors to allow transmission to other devices.

In the right hearing device, the right sensor potential $P_{right}$ and right ground potential $HD_{rGND}$ is fed to wireless transmitter unit Tx, e.g. comprising an analogue to digital (AD) converter providing sensor signal $\Delta V_{right}$ representative of the right sensor potential $P_{right}$ and/or appropriate modulation/coding circuitry. In an embodiment, the antenna and transceiver circuitry is adapted to establish a digital link, e.g. according to Bluetooth (e.g. Bluetooth Low Energy) or other low power wireless transmission technology (e.g. ZigBee). In an embodiment, the wireless link is based on near-field communication, e.g. based on capacitive or inductive coupling between corresponding antenna elements in the first and second parts of the hearing assistance system. The left hearing device ($HD_{left}$) comprises antenna and transceiver circuitry allowing the reception of the voltage difference $\Delta V_{right}$ from the right hearing device. The transceiver of the left hearing device comprises wireless receiver Rx, e.g. comprising a low-noise amplifier and/or demodulation/decoding circuitry to extract right reference potential $P_{right}$ by addition of left hearing device ground $P(HD_{lGND})$. In the embodiment of FIG. 3, the EOG-signal voltage difference $\Delta P_{EOG}$ is generated by an amplifier of the amplifier and processing unit (COMPU) as described in connection with FIG. 1A and/or 2A. The resulting estimate of gaze angle $\Delta\theta$ is forwarded to the signal processors (SPU) of the respective left and right hearing devices for further processing and/or as inputs to the control of a processing algorithm (e.g. in a beamformer filtering unit, cf. WGTU in FIG. 7). The estimate of gaze angle $\Delta\theta$ is forwarded directly to the signal processor of the left hearing device and via the wireless link WL (signal $\Delta V_\theta$) to the signal processor of the right hearing device.

Preferably, the left and right hearing device ground potentials $P(HD_{lGND})$ and $P(HD_{rGND})$ are essentially equal. In an embodiment, the left and right hearing devices are configured to provide that the left and right hearing device ground potentials $P(HD_{lGND})$ and $P(HD_{rGND})$ are virtual ground potentials defined by the body of the user via capacitive coupling to the ground potential of the earth, as e.g. used in communication via body networks, cf. e.g. EP2997893A1.

FIG. 4 schematically illustrates the capture of electrooculography signals from a user's eye using beamforming according to the present disclosure. FIG. 4 shows an eye (Eye) comprising a pupil (Pupil) and eye liquid enclosed in the eye ball. In the example of FIG. 4, the pupil is located in a left side of the eye ball reflecting a particular eye gaze angle $\Delta\theta$ (cf. e.g. FIG. 2B). The particular eye gaze angle is characterized in a particular distribution of charge in the eye liquid as symbolically indicated by '+' and '−' in the left and right sides, respectively, of the eye ball. The resulting potentials (or scaled values thereof) are sensed by electric potential sensors (EPS1, EPS2) of the electrooculography signal capture system. The electric potential sensors (EPS1, EPS2) sense potentials P1 and P2, respectively. The sensed potentials are referred to a reference potential Pref picked up by electric potential sensor EPSref (comprising a reference electrode, possibly located spatially dislocated from the 'measurement' electrodes (EPS1, EPS2)). In the embodiment of FIG. 4, the electric potential sensors (EPS1, EPS2, EPSref) are e.g. located on a housing of an ITE part (e.g. of a hearing aid) located in an ear canal (Ear canal) of the user in contact with the inner wall of the ear canal. The sensed (or measured) potentials are fed to differential buffers (DBUF, e.g. implemented as respective AD-converters, cf. e.g. components A/D in FIG. 2A). The differential buffers (DBUF) provide respective voltage difference signals ($\Delta P1$ and $\Delta P2$) as (possibly scaled (e.g. amplified)) differences between the respective electric potentials and the reference potential ($\Delta P1=(P1-Pref)*A$ and $\Delta P2=(P2-Pref)*A$, where A is a scaling factor, e.g. $A\geq 1$, e.g. $A\geq 10$).

The voltage difference signals ($\Delta P1$ and $\Delta P2$) are fed to electric potential beamformer (BF) which provides two different beamformed signals ($S_{BF1}$, $S_{BF2}$), which are formed as a weighted combination of the voltage difference signals $\Delta P_i$, $i=1, 2$. In an embodiment, the beamformed signals $S_{BFj}$ are linear combinations of the voltage difference signals $\Delta P_i$, i.e. $S_{BF1}=w_{11}*\Delta P_1+w_{12}*\Delta P_2$, and $S_{BF2}=w_{21}*\Delta P_1+w_{22}*\Delta P_2$, where the beamformer weights $w_{ji}$ are generally complex, frequency dependent values (e.g. fixed values for a fixed beamformer and time dependent values for an adaptive beamformer).

The beamformer filtering coefficients $w_{ij}$ may e.g. be determined as is customary in the field of antenna array circuits, cf. e.g. Wikipedia entries on 'Antenna arrays' (https://en.wikipedia.org/wiki/Antenna_array) or 'Dipole antenna' (https://en.wikipedia.org/wiki/Dipole_antenna), or a standard textbook on antenna arrays (e.g. 'Antenna Arrays: A Computational Approach' by Randy L. Haupt, Wiley-IEEE Press, May 2010). The electric potential beamformers may e.g. have an equivalent structure to a generalized sidelobe canceller (GSC). In an embodiment, the electric potential beamformers may comprise a minimum variance distortionless response (MVDR) beamformer, which (ideally) keeps signals from a target direction unchanged, while attenuating signals from other directions maximally Reference is further made to [Van Veen & Buckley; 1988] providing an overview of antenna array beamforming, in particular to FIGS. 2.1(a) and (b), where the basic terminology and concepts are defined and to equations (2.1), (2.2) and (2.3) as the general beamforming algorithm. The same beamforming methods can be used regardless of the 'contents' or meaning of the data (be they electromagnetic fields, acoustic vibrations or electric potentials) picked by a configuration (e.g. an array) of 'sensors' (be they antennas or microphones or electric potential sensors). Beamformer weights are designed in the same way that FIR-filter weights are determined, i.e. by defining an ideal spatial filter (in contrast to magnitude response in FIR-filters) and approximate with a FIR optimization algorithm, e.g. the Remez algorithm or any of the suggestions of [Elliott; 1987], cf. chapter 2. Examples from [Van Veen & Buckley; 1988] of different beamforming techniques that may be used in the present context:

III. DATA INDEPENDENT BEAMFORMING (page 11 ff.):
    A. *Classical Beamforming*, cf. page 11-12 and the example in FIG. 3.1 with 16×16 array of sensors.
    B. *General Data Independent response design*, cf. page 12-13. May be used in connection with a scenario as illustrated in FIG. 4 where we want to cover an area around the eyes and at the same time suppress signals from another direction, like a combination of bandpass and bandstop filters.
  IV. STATISTICALLY OPTIMUM BEAMFORMING (page 13 ff.). Weights chosen based on the statistics of the data received from the array.
    A. *Multiple sidelobe canceller*, cf. page 13-14.
    D. *Linearly Constrained Minimum Variance Beamforming* (LMCV), cf. page 14-17. The response of the beamformer is constrained, so signals from the direction of interest are passed with specified gain and phase. The weights are chosen to minimize output variance or power subject to the response constraint. E.g. according to equations (4.2) and (4.3). See example in FIG. 4.2 (page 16).
  V. ADAPTIVE ALGORITHMS FOR BEAMFORMING (page 17 ff.). RLS or LMS algorithms.

In an embodiment, the beamforming technology is based on phased arrays, and is used to scan a certain part of the skull (e.g. one eye at the time) by appropriately adjusting delays and weights (as e.g. described in sections III, IV and V of [Van Veen & Buckley; 1988]).

The beamformer weights ($w_1$, $w_{12}$) and ($w_{21}$, $w_{22}$) may e.g. be representative of first and second beam patterns BP1 and BP2, respectively, as schematically illustrated in FIG. 4, intended to illustrate beam patterns that do not attenuate signals from the respective target directions (i.e. towards the maximum ('+' (BP1)) and minimum ('−' (BP2)) electric potential, respectively, e.g. towards each 'end' of the eye ball). The first and second beam patterns BP1 and BP2 are further adapted to attenuate electric potentials from the respective other target direction (BP1 attenuates signals from the right end of the eye ball ('−') and BP2 attenuates signals from the left end of the eye ball ('+'). The beamformed signals ($S_{BF1}$, $S_{BF2}$) are fed to processor (PRO) providing electrooculography signal ($\Delta P_{EOG}$) from one eye of the user ($\Delta P_{EOG} = S_{BF1} - S_{BF2}$). The functionality of the components of the system for capturing electrooculography signals illustrated in FIG. 4 is equivalent to the one shown in FIG. 2A, apart from the further processed output estimate a current eye gaze angle, $\Delta\theta$, in FIG. 2A.

Figure 5:
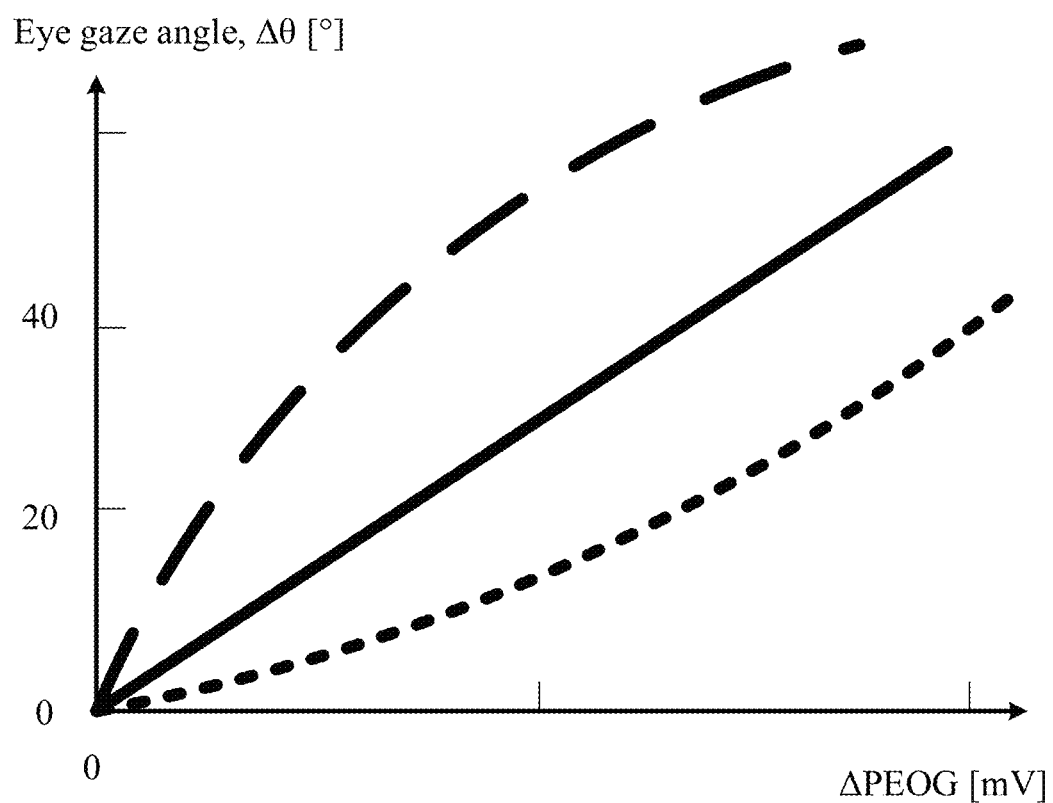
FIG. 5 shows an exemplary dependence of gaze angle [°] on EOG voltage [mV]

The electrooculography signal ($\Delta P_{EOG}$) provided in FIG. 4 is representative of a current eye gaze, and may be used to estimate a current eye gaze angle $\Delta\theta$, e.g. using a stored algorithm or table of corresponding values of $\Delta P_{EOG}$ and $\Delta\theta$ (e.g. measured or estimated), cf. schematic dependencies illustrated in FIG. 5. Such further processing may also form part of the processor (PRO), thereby providing an output equivalent to the embodiment of FIG. 2A.

Figure 6:
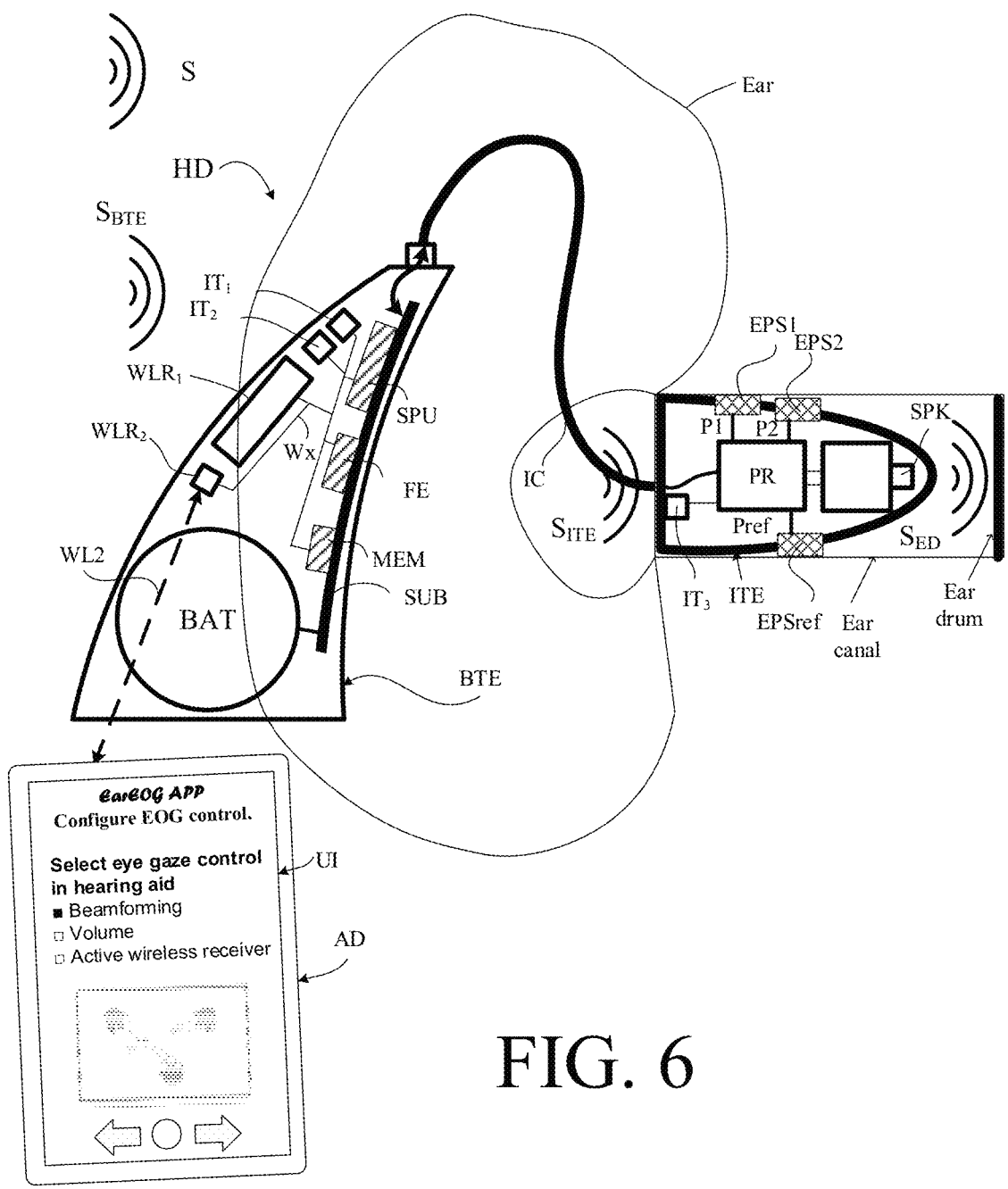
FIG. 6 shows an embodiment of a hearing system comprising a hearing device and an auxiliary device in communication with each other according to the present disclosure.

The estimation of eye gaze angle may be activated (e.g. automatically, by the user) in a hearing device in a specific electroculography mode of operation, e.g. from a remote control, such as a smartphone, see e.g. FIG. 6.

In the exemplary system of FIG. 4, two electric potential sensors (e.g. electrodes) are used. In a more general system, three or more, e.g. 4 or 6 sensors may be used. In general, the number of sensors Ns should be adapted to the specific application.

In an embodiment, the electric circuitry is configured to provide that the two or more beamformers are adaptive and configured to maximize a difference between the beamformed signals.

In practice, measurement artifacts, such as drift over time of the EOG signal and/or muscular activity may be significant. In that case, measures to compensate for that may preferably be taken, e.g. using Kalman filtering, cf. e.g. [Manabe & Fukamoto; 2010].

FIG. 5 shows an exemplary dependence of gaze angle [°] on EOG voltage [mV]. Three different exemplary courses of $\Delta\theta(\Delta PEOG)$ are shown, a linear (solid line) and two curved (dotted and dashed, respectively) graphs. Preferably, such data are available for a given user, e.g. provided in a prior calibration session, or estimated based on empirical data, possibly in dependence on a user's facial characteristics.

FIG. 6 shows an embodiment of a hearing system comprising a hearing device and an auxiliary device in communication with each other according to the present disclosure. FIG. 6 illustrates an exemplary hearing aid (HD) comprising a BTE-part (BTE) adapted for being located behind pinna and a part (ITE) comprising a housing accommodating one or more electric potential sensors (EPS1, EPS2, EPSref) for capturing electric potentials (P1, P2, Pref respectively) of the body (e.g. comprising sensing electrodes, and possibly associated electric circuitry for generating a corresponding sensing voltage). The ITE-part may, as shown in FIG. 6, further comprise an output transducer (e.g. a loudspeaker/receiver, SPK) adapted for being located in an ear canal (Ear canal) of the user and to provide an acoustic signal (providing, or contributing to, acoustic signal SED at the ear drum (Ear drum)). In the latter case, a so-called receiver-in-the-ear (RITE) type hearing aid is provided. The BTE-part (BTE) and the ITE-part (ITE) are connected (e.g. electrically connected) by a connecting element (IC), e.g. comprising a number of electric conductors. Electric conductors of the connecting element (IC) may e.g. have the purpose of transferring electrical signals from the BTE-part to the ITE-part, e.g. comprising audio signals to the output transducer, or for transferring potentials or voltage differences from the electric potential sensors on the ITE part to a processor (cf. e.g. SPU in FIG. 6) in the BTE-part. The BTE part may also or alternatively comprise one or more electric potential sensors (EPS), and optionally a reference potential electrode. In the embodiment shown in FIG. 6, the ITE-part comprises two electric potential sensors (EPS1, EPS2) and a reference sensor (EPSref). The ITE part further comprises a processor (PR) for distributing and optionally processing signals of the ITE-part (e.g. signal from the input transducer (IT3), from the electric potential sensors (EPS1, EPS2, EPSref), to the loudspeaker (SPK) and to/from the connecting element (IC)). In an embodiment, the processor (PR) of the ITE part is configured to provide the EOG signals as amplified (possibly digitized) voltage differences ($\Delta P1$, $\Delta P2$) between the two potentials (P1, P2) and the reference potential (Pref). The resulting EOG-signals may e.g. be transmitted (transferred) to the BTE-part and used there via a conductor of the connecting element (IC), or further processed (e.g. beamformed) in processor (PR) depending on the practical partition of the system. The BTE part (BTE) comprises an input unit (IU in FIG. 3) comprising two input transducers (e.g. microphones) ($IT_1$, $IT_2$) each for providing an electric input audio signal representative of an input sound signal ($S_{BTE}$) from the environment. In the scenario of FIG. 6, the input sound signal $S_{BTE}$ includes a contribution from sound source S (and possibly additive noise from the environment). The hearing aid (HD) of FIG. 6, e.g. an input unit (IU in FIG. 2), further comprises two wireless transceivers ($WLR_1$, $WLR_2$) for transmitting and/or receiving respective audio and/or information signals and/or control signals (including potentials or voltages provided by the electric potential sensors (EPS)). The hearing aid (HD) further comprises a substrate (SUB) whereon a number of electronic components are mounted, functionally partitioned according to the application in question (analogue, digital, passive components, etc.), but including a configurable signal processor (SPU), e.g. comprising a processor for executing a number of processing algorithms, e.g. to compensate for a hearing loss of a wearer of the hearing device), a front end IC (FE) for interfacing to the input and output transducers, etc. and a memory unit (MEM) coupled to each other and to input and output transducers and wireless transceivers via electrical conductors Wx. The mentioned functional units (as well as other components) may be partitioned in circuits and components according to the application in question (e.g. with a view to size, power consumption, analogue vs. digital processing, etc.), e.g. integrated in one or more integrated circuits, or as a combination of one or more integrated circuits and one or more separate electronic components (e.g. inductor, capacitor, etc.). The configurable signal processor (SPU) provides a processed audio signal, which is intended to be presented to a user. In the embodiment of a hearing device in FIG. 6, the ITE part (ITE) comprises an input transducer (e.g. a microphone) ($IT_3$) for providing an electric input audio signal representative of an input sound signal $S_{ITE}$ from the environment (including from sound source S) at or in the ear canal. In another embodiment, the hearing aid may comprise only the BTE-microphones ($IT_1$, $IT_2$). In another embodiment, the hearing aid may comprise only the ITE-microphone ($IT_3$). In yet another embodiment, the hearing aid may comprise an input unit ($IT_4$) located elsewhere than at the ear canal in combination with one or more input units located in the BTE-part and/or the ITE-part. The ITE-part may further comprise a guiding element, e.g. a dome or equivalent, for guiding and positioning the ITE-part in the ear canal of the user.

The hearing aid (HD) exemplified in FIG. 6 is a portable device and further comprises a battery, e.g. a rechargeable battery, (BAT) for energizing electronic components of the BTE- and possibly of the ITE-parts.

In an embodiment, the hearing device (HD) of FIG. 6 comprises a system for capturing electrooculography signals, e.g. an eye gaze estimation system, according to the present disclosure.

The hearing aid (HD) may e.g. comprise a directional microphone system (including a beamformer filtering unit) adapted to spatially filter out a target acoustic source among a multitude of acoustic sources in the local environment of the user wearing the hearing aid, and to suppress 'noise' from other sources in the environment. The beamformer filtering unit may receive as inputs the respective electric signals from input transducers $IT_1$, $IT_2$, $IT_3$ (and possibly $IT_4$) (or any combination thereof) and generate a beamformed signal based thereon. In an embodiment, the directional system is adapted to detect (such as adaptively detect) from which direction a particular part of the microphone signal (e.g. a target part and/or a noise part) originates. In an embodiment, the beam former filtering unit is adapted to receive inputs from a user interface (e.g. a remote control or a smartphone) regarding the present target direction. In an embodiment, the beamformer filtering unit is controlled or influenced by signals from the sensing electrodes (or processed versions thereof, e.g. EOG-signals representative of eye gaze of the user). In an embodiment, the direction of a beam (or a 'zero point) of the beamformer filtering unit is thereby controlled or influenced. In another embodiment, the input from one of the wireless receivers is selected based on signals from the sensing electrodes (or processed versions thereof, e.g. EOG-signals representative of eye gaze of the user). The memory unit (MEM) may e.g. comprise pre-defined (or adaptively determined) complex, frequency dependent constants ($W_{ij}$) defining predefined (or adaptively determined) or 'fixed' beam patterns (e.g. omni-directional, target cancelling, pointing in a number of specific directions relative to the user), together defining the beamformed signal $Y_{BF}$.

The hearing aid of FIG. 6 may constitute or form part of a hearing aid and/or a binaural hearing aid system according to the present disclosure. The processing of an audio signal in a forward path of the hearing aid (the forward path including the input transducer(s), the signal processor, and the output transducer) may e.g. be performed fully or partially in the time-frequency domain. Likewise, the processing of signals in an analysis or control path of the hearing aid may be fully or partially performed in the time-frequency domain.

The hearing aid (HD) according to the present disclosure may comprise a user interface UI, e.g. as shown in FIG. 6 implemented in an auxiliary device (AD), e.g. a remote control, e.g. implemented as an APP in a smartphone or other portable (or stationary) electronic device. In the embodiment of FIG. 6, the screen of the user interface (UI) illustrates an EarEOG APP, with the subtitle 'Select eye gaze control in hearing aid' (upper part of the screen). Possible functions that can be selected by the user—via the APP—for control via eye gaze are exemplified in the middle part of the screen. The options are 'Beamforming', 'Volume' and 'Active wireless receiver'. In the screen shown in FIG. 6, the option 'Beamforming' has been selected (as indicated by solid symbols ■, and illustrated by the graphical symbol beneath the options). The arrows at the bottom of the screen allow changes to a preceding or a proceeding screen of the APP, and a tab on the circular dot between the two arrows brings up a menu that allows the selection of other APPs or features of the device. In an embodiment, the APP is configured to provide an (possibly graphic) illustration of the currently selected or activated beamformer, or volume setting, or wireless connections. The 'Beamforming' and 'Active wireless receiver' may e.g. be controlled by horizontal eye gaze. 'Volume' may e.g. be controlled via vertical eye gaze.

The auxiliary device (AD) and the hearing aid (HD) are adapted to allow communication of data, including data representative of the currently selected function to be controlled via eye gaze to the hearing aid via a, e.g. wireless, communication link (cf. dashed arrow WL2 in FIG. 6). The communication link WL2 may e.g. be based on far field communication, e.g. Bluetooth or Bluetooth Low Energy (or similar technology), implemented by appropriate antenna and transceiver circuitry in the hearing aid (HD) and the auxiliary device (AD), indicated by transceiver unit WLR2 in the hearing aid.

The hearing aid may comprise a number of wireless receivers (e.g. symbolized by WLR, in FIG. 6), or may be arranged to receive signals on configurable channels, for receiving different audio signals and/or other signals from a number of transmitters, e.g. from a number of wireless microphones. In an embodiment, reception of signals from a given transmitter may be controlled by the user via eye gaze (here derived from EarEOG-signals), cf. mode 'active wireless receiver' of the EarEOG APP.

The aspects of eye gaze control described in connection with FIG. 6 are intended to exemplify the use of an eye gaze estimation system according to the present disclosure. The aspects are discussed in further detail in our co-pending European patent application 16205776.4, published as EP3185590A1.

Figure 7:
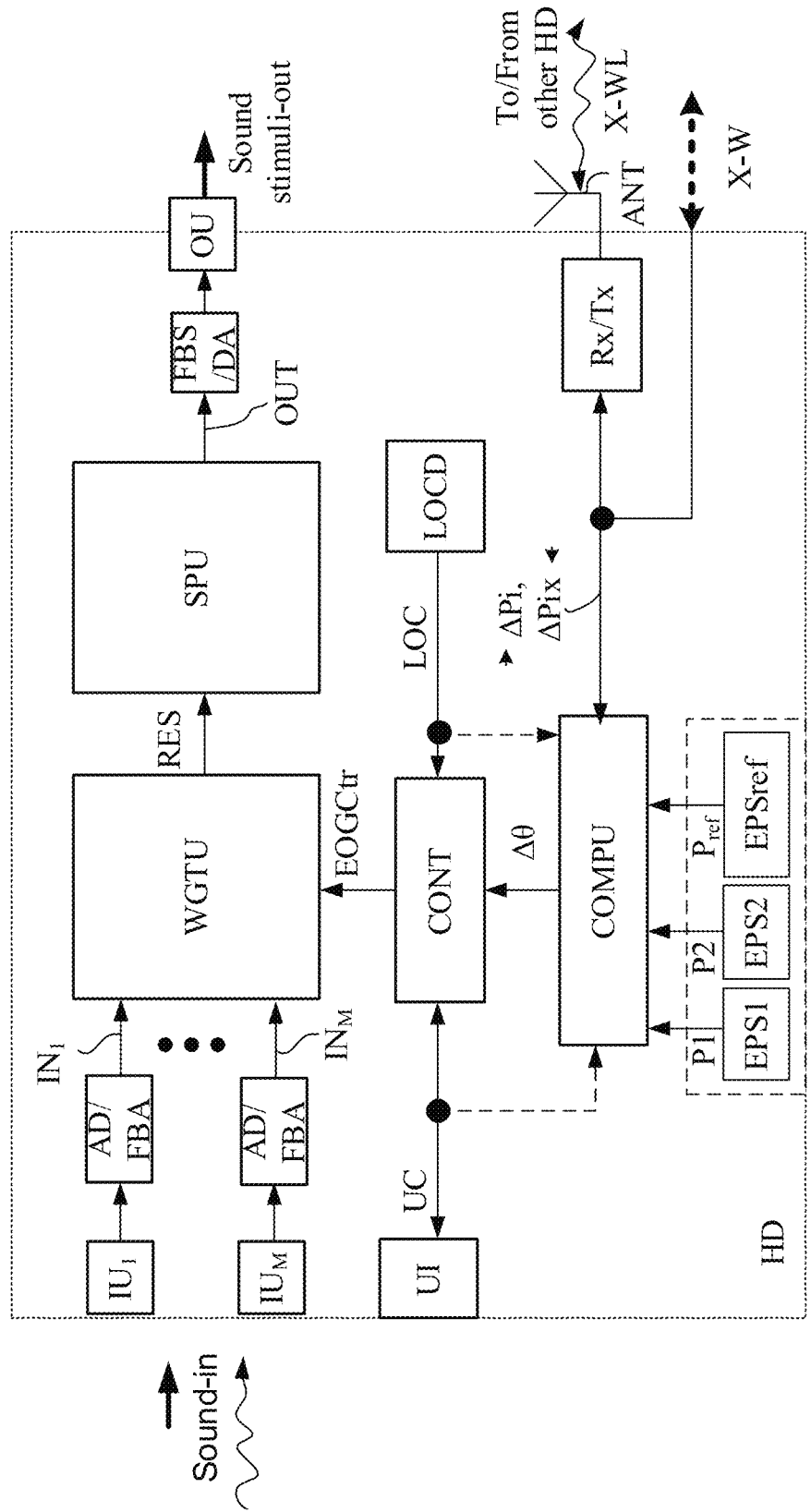
FIG. 7 shows an embodiment of a hearing device according to the present disclosure.

FIG. 7 shows an embodiment of a hearing device according to the present disclosure. The hearing device, e.g. a hearing aid, (HD) comprises a forward path from a number M of input units ($IU_1, \ldots, IU_M$) for picking up sound or receiving electric signals representing sound (Sound-in') to an output unit (OU) for providing stimuli (Sound stimuli-out') representing said sound and perceivable as sound by a user wearing the hearing device. The forward path further comprises a number M of analogue to digital converters (AD) and analysis filter banks (FBA) operationally coupled to each their input unit ($IU_1, \ldots, IU_M$) and providing respective digitized electric input signals $IN_1, \ldots, IN_M$ in a time-frequency representation, each comprising a number K of frequency sub-band signals $IN_1(k,m), \ldots, IN_M(k,m)$, k and m being frequency and time indices, respectively, $k=1, \ldots, K$. The forward path further comprises a weighting unit (WGTU) (or beamformer filtering unit BFU) receiving the electric input signals as inputs and providing a resulting signal RES as a weighted combination of the M electric input signals. In other words, $RES=IN_1(k,m)*w_1(k,m), \ldots, IN_M(k,m)*w_M(k,m)$, where $w_i$, $i=1, \ldots, M$, are real or complex (in general, time and frequency dependent) weights. The forward path further comprises a signal processor (SPU) for further processing the resulting signal RES and providing a processed signal OUT. The signal processor (SPU) is e.g. configured to apply a level and/or frequency dependent gain or attenuation according to a user's needs (e.g. hearing impairment). The forward path further comprises a synthesis filter bank (FBS) for converting frequency sub-band signals OUT to a single time-domain signal, and optionally a digital to analogue conversion unit (DA) to convert the digital processed time-domain signal to an analogue electric output signal to the output unit (OU).

The hearing device (HD) comprises a system for capturing electrooculography signals, e.g. an eye gaze estimation system, according to the present disclosure, for picking up bio signals from the user's body. The system comprises an electric potential sensor part adapted for being located at or in an ear and/or for fully or partially for being implanted in the head of a user. The sensor part comprises a number of electrical potential sensors (EPSi) for sensing an electrical potential (Pi) from the body of the user (here i=1, 2), in particular from the head, e.g. due to brain activity or eye movement. The sensor part may further comprise a reference sensor electrode (EPSref) for providing a reference voltage (Pref). The electrical potential sensor (EPSx) may e.g. comprise an electrode configured to contact skin or tissue of the user's head, when the electric potential sensor part (e.g. the hearing device) is operationally mounted on the user (e.g. in an ear canal) or implanted in the head of the user. The eye gaze estimation system further comprises an amplifier and processing unit (COMPU), in the form of electronic circuitry coupled to the electrical potential sensor part to provide an amplified EOG signal in the form of an estimated eye gaze angle $\Delta\theta$ (see e.g. FIG. 1B). The amplifier, e.g. comprising a differential buffer, e.g. a differential amplifier and/or an analogue to digital converter, receives potentials P1, P2, $P_{ref}$ from electric potential sensors of the hearing device (EPS1, EPS2, EPSref) as well as voltage differences relative to a reference potential ($\Delta$Pix, i=1, 2) from a corresponding contralateral hearing device either via wireless link X-WL or wired connection X-W. The amplifier further receives a reference potential $P_{ref}$ from reference electrode (EPSref), either located in the hearing device or elsewhere on or in the head of the user. Potential differences ($\Delta$Pi, i=1, 2) representing locally captured potentials relative to the reference potential $P_{ref}$ are transmitted to the contralateral hearing device.

The hearing device comprises at least two electrical potential sensor (EPS) (EPS1, EPS2), each providing a potential (P1, P2) representing an electro-oculography potential. The two potentials are used as inputs to an electric potential beamformer as discussed in connection with FIG. 4. In an embodiment, an EOG signal representative of a current eye gaze angle of the user is estimated from a difference between the two beamformed potentials (SBF1, SBF2) (originating from sensors located in the 'local' hearing device) provided by the electric potential beamformer as discussed in connection with FIG. 4. In an embodiment, a current eye gaze angle is estimated based on monaural data (from the at least two sensors in the same hearing device) in each of a left and a right hearing device. This may have the advantage of avoiding the transfer of potentials from one hearing device to the other (i.e. to avoid a direct electrical cable or a wireless link between the left and right ears). In an embodiment, the results of the two monaurally determined estimates may then be exchanged between the hearing devices, and an average or other combination of the two estimates may be determined and used for control of processing algorithms in each of the hearing devices.

In an embodiment, at least one (such as all) of the input units comprises an input transducer, e.g. a microphone. In an embodiment, at least one (such as all) of the input units comprises a wireless transceiver, e.g. a wireless receiver, e.g. configured to receive a signal representative of sound picked up by a remote (wireless) microphone.

The hearing device may further comprise or be coupled to a location sensor unit (LOCD) providing location data (LC) representative of a current location of the user, e.g. representative of the user's head, e.g. in a fixed coordinate system (e.g. relative to a specific location, e.g. a room). In an embodiment, the location sensor comprises a head tracker. In an embodiment, the location sensor comprises an accelerometer and a gyroscope. In an embodiment, the location sensor comprises a 9 degree of freedom sensor, comprising a 3D accelerometer, a 3D gyroscope, and a 3D magnetometer.

In an embodiment, the hearing device further comprises a wireless transceiver and appropriate antenna circuitry (ANT, Rx/Tx) allowing the mentioned reception of electric potentials (Pix) (or voltage differences ($\Delta$Pix) referring the potentials to a reference) from and transmission of such signals (Pi, $\Delta$Pi) to a contra-lateral hearing device, e.g. representative of eye movement, via a wireless link (X-WL) or wired connection (X-W), cf. waved and dotted straight, arrowed lines denoted 'To/From other HD' in FIG. 7. The electric potential differences ($\Delta$Pix) from the contra-lateral hearing device are fed to the amplifier and processing unit (COMPU) and compared to the corresponding locally generated potentials (P1, P2).

The hearing device further comprises a control unit (CONT) for providing a control signal for controlling a function of the hearing device based on the EarEOG signal(s), e.g. selecting wireless reception from a particular person, or as exemplified in FIG. 7, controlling the beamformer unit (WGTU), e.g. selecting one of a number of predefined beamformers in dependence of an eye gaze control signal EOGCtr. The predefined beamformers may e.g. be stored in a memory of the hearing device, e.g. as sets of beamformer filtering coefficients, each corresponding to a given one of a number of predefined locations of a sound source of interest (relative to the user). The control unit (CONT) and/or the amplifier and processing unit (COMPU, cf. dashed line input of LOC) is configured to combine possible location data LOC (e.g. head location data) with the estimated gaze angle $\Delta\theta$. The control unit (CONT) may comprise a Kalman filter for filtering location data and/or estimated eye gaze angles to minimize the effect of drift. The hearing device further comprises a user interface (UI, and control signal UC) for controlling the use of eye gaze to control various functional parts of the hearing device (and possibly displaying data relevant for eye gaze control, cf. e.g. FIG. 6). Based on inputs UC, LOC and estimated eye gaze angle $\Delta\theta$, control unit (CONT) provides control signal EOGCtr to the beamformer unit (WGTU).

In a specific mode of operation (a 'learning mode'), the calculation unit may be configured to determine locations representing preferred eye gaze directions of the user. The locations (e.g. represented in a fixed coordinate system) may be stored in a memory of the hearing device (or in an auxiliary device, e.g. a smartphone or the like). The locations may e.g. be displayed via a user interface (e.g. via an app of a smartphone).

Figure 8:
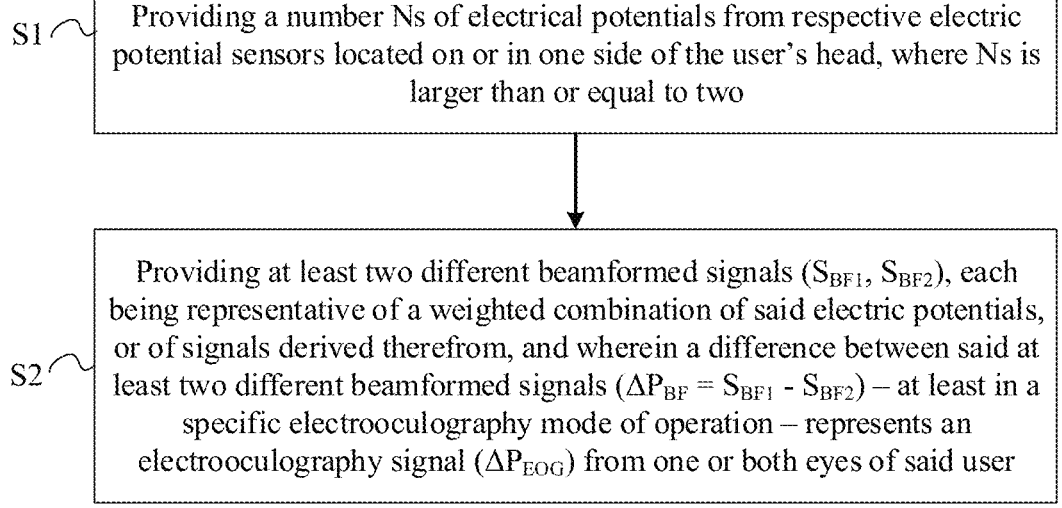
FIG. 8 shows a flow diagram for a method of estimating an eye gaze angle based on capture of electrooculography signals according to an embodiment of the present disclosure, FIG. 9A schematically shows a configuration of an eye gaze estimation system according to the present disclosure.

FIG. 8 shows a flow diagram for a method of estimating an eye gaze angle based on capture of electrooculography signals according to an embodiment of the present disclosure. The method comprises a) providing a number Ns of electrical potentials from respective electric potential sensors located on or in one side of the user's head, where Ns is larger than or equal to two. The method further comprises b) providing at least two different beamformed signals (SBF1, SBF2), each being representative of a weighted combination of said electric potentials, or of signals derived therefrom, and wherein a difference between said at least two different beamformed signals ($\Delta P_{BF}=S_{BF1}-S_{BF2}$)—at least in a specific electrooculography mode of operation— represents an electrooculography signal ($\Delta P_{EOG}$) from one or both eyes of said user. In an embodiment, the method comprises a prior calibration step for calibrating an estimation of eye gaze angle from said difference between said at least two different beamformed signals. In an embodiment, the method comprises estimating an eye gaze angle from the captured electrooculography signals. In an embodiment, the method comprises controlling a function of an electronic device, e.g. a hearing aid, based on the captured electrooculography signals.

Monaural, Single Electrode EOG:

Up till now, it has been assumed that the measurement of Electroocculography (EOG) signals signals (e.g. to monitor eye gaze of a user) requires a differential measurement, e.g. from two independent electrodes located at left and right eyes of a user (or in left and right ears of a user, cf. e.g. EP3185590A1) or a directional system utilizing at least two electrodes located at the same eye or ear of a user (as proposed in the present application).

The present inventor has uncovered that it is possible to capture an EOG signal (e.g. representative of eye gaze) from a single monitoring electrode e.g. located at one of the eyes (or ears) of the user. In particular, capacitive sensors (so-called 'electric potential sensors', EPS) lend themselves to such application, e.g. sensors produced by Plessey Semiconductors (cf. e.g. http://www.plesseysemiconductors.com/).

Measurement at one location is advantageous, in particular in wearable devices, such as ear plugs or hearing aids, because it removes the need to transmit measurements from the pick-up locations (e.g. left right eyes or ears) to other devices for determining a resulting EOG-value.

Figure 9A:
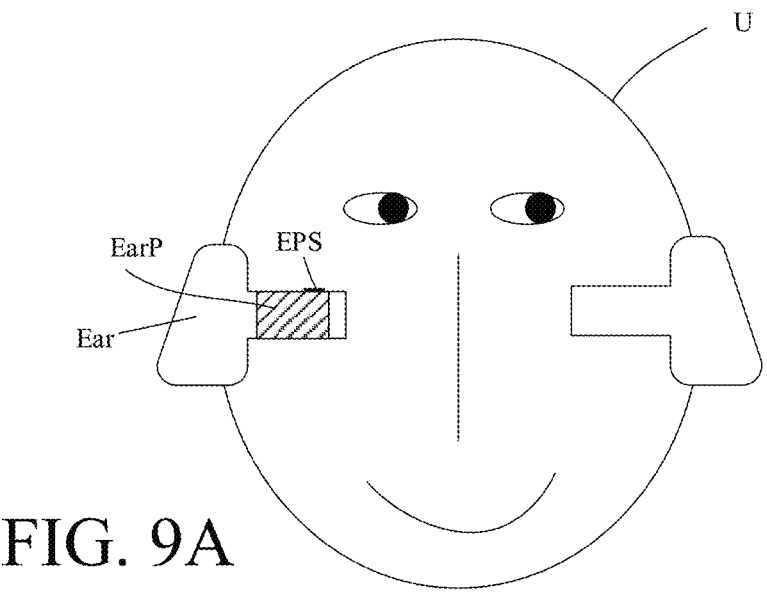
FIG. 9B shows a schematic diagram of an exemplary electric potential sensor (EPS) with associated electronic circuitry, wherein an internal current is generated and modulated by the electrical field sensed by the electrode, the EPS sensor forming part of the eye gaze estimation system of FIG. 9A, and FIG. 10 schematically illustrates a scenario where a portable electrooculography (EOG) signal capture system comprising a sensor array comprising three sensors (e.g. electric potential sensors) is located at an ear of a user.
Figure 9B:
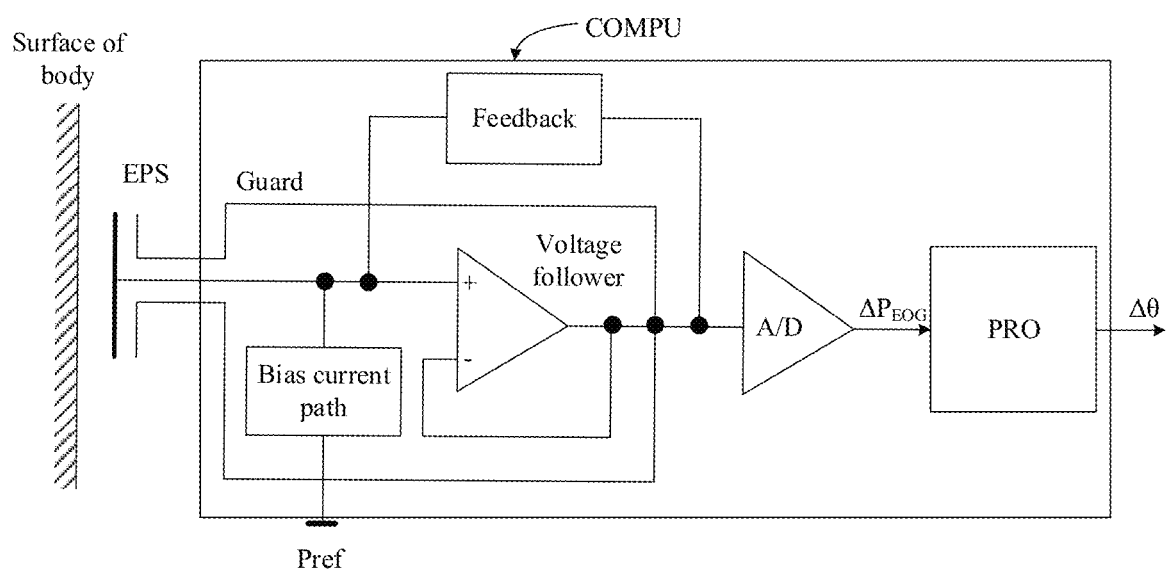

FIG. 9A schematically shows a configuration of an eye gaze estimation system according to the present disclosure. The user (U) wears a portable electrooculography (EOG) signal capture system comprising, e.g. an ear piece (EarP), comprising a single electric potential sensor (EPS) configured to be in contact with the users skin, e.g. as illustrated in FIG. 9A, located in an ear canal at an (here the right) ear of the user. The eye gaze estimation system further comprises electronic circuitry (COMPU), as illustrated in FIG. 9B, electrically coupled to the electrical potential sensor (EPS) and configured to determine a single channel amplified output ($\Delta P$) representative of a difference between said left and right electrical potentials. The single channel amplified output ($\Delta P$) represents—at least in a specific electrooculography (EOG) mode of operation—an EOG signal ($\Delta P_{EOG}$). In the embodiment of FIG. 9B, the electric circuitry comprises an analogue to digital converter (A/D) for providing an amplified, digitized version of the signal provided by the (single) electrical potential sensor (EPS). The electronic circuitry (COMPU) further comprises a signal processor (PRO) configured to estimate an eye gaze angle ($\Delta \theta$) based on the (possibly further processed, e.g. filtered) EOG signal ($\Delta P_{EOG}$), as e.g. discussed in connection with FIG. 5.

In the electrical potential sensor (EPS) of FIG. 9B, an internal current (cf. Bias current path) is generated and modulated by the electrical field sensed by the electrode. The EPS sensor is e.g. discussed in EP3185590A1. The reference potential Pref may e.g. be a potential relative to a battery voltage. The single electrode solution may e.g. alternatively work using a virtual ground from the user's body (or from the earth or other stable potential surrounding the user).

Body networks using virtual ground is e.g. discussed in EP2997893A1.

In a hearing device, a capacitive electrode may be formed by coating techniques, e.g. on a generic housing, or on a dome or instant fit device (or on a customized housing).

Beamforming. Inverse Model.

Figure 10:
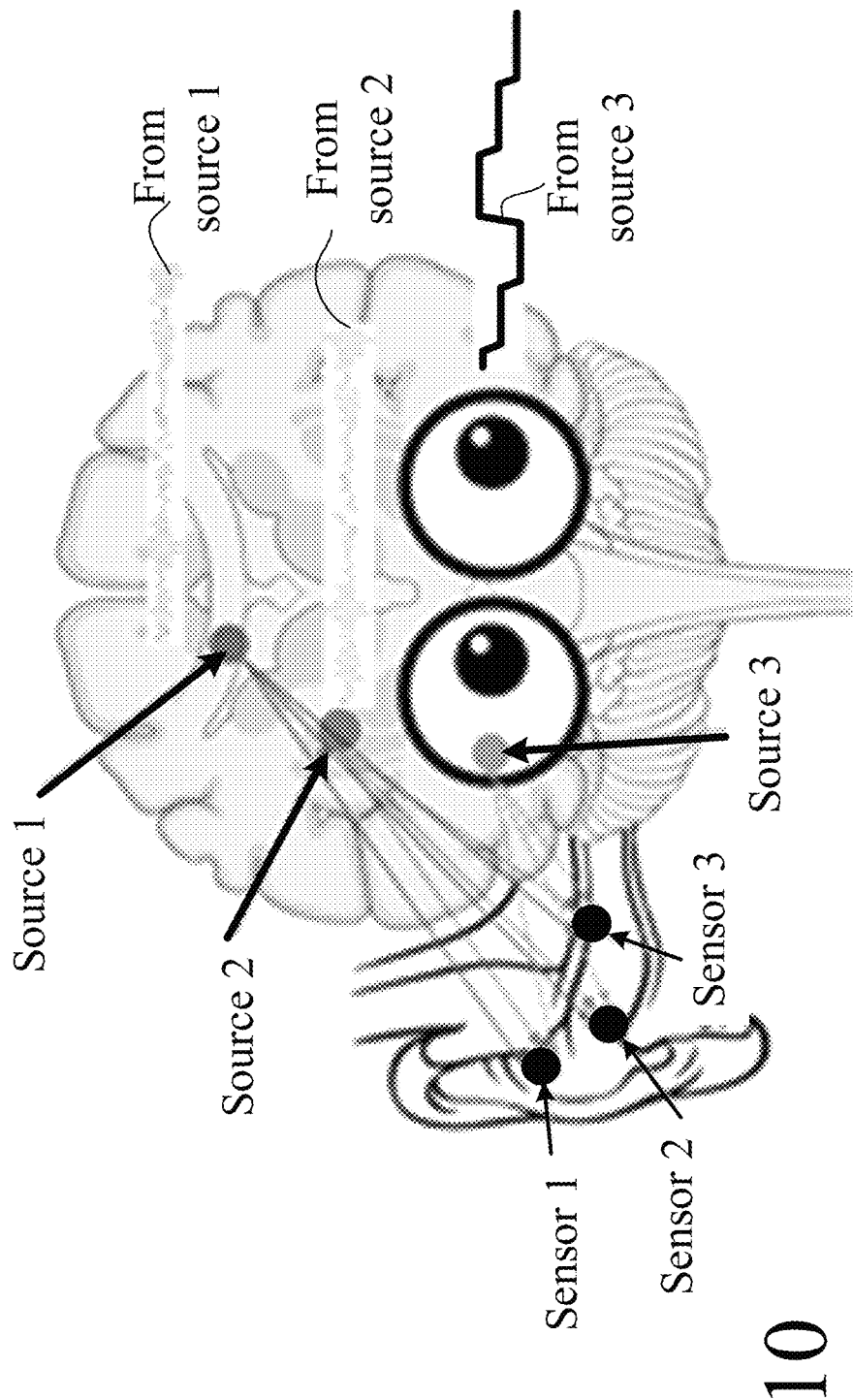

FIG. 10 schematically illustrates a scenario where a portable electrooculography (EOG) signal capture system comprising a sensor array comprising three sensors (e.g. electric potential sensors) is located at an ear of a user.

Given a number of sensors (e.g. electric potential sensors) spatially distributed in an array and a number of sources contributing to the signal received in all sensors, the contribution of each source to the captured signal can be reconstructed via calculating an Inverse Model (i.e. from observed data to source location). Three signal sources (denoted Source 1, 2, 3 in FIG. 10) are indicated as sources of electric potentials to be picked up by the three sensors (denoted Sensor 1, 2, 3 in FIG. 10). The number of signal sources may be smaller or larger than three. Likewise, the number of sensors may be smaller or larger than three. Exemplary signals from each of the sources (Source 1, 2, 3) are indicated to the right of the respective sources (denoted 'From source 1', 'From source 2', and 'From source 3', respectively in FIG. 10). Signals 'From source 1' and 'From source 2' are indicated as relatively fast varying low amplitude signals with occasional short segments with larger amplitude, e.g. typical EEG signals (with occasional artifacts, e.g. from eye blinks or the like). Signal 'From source 3' is indicated as a relatively stable multistep signal, e.g. typical of an EOG signal. In an embodiment, the beamformer is intended to 'focus' on source 3 (EOG).

The observed data at the sensors (here e.g. electric potentials, or electric potential differences) can be considered as $$X=s*h$$

Where X is the data matrix of all sensors across time, s is a single source in question (e.g. one of Source 1, 2, 3) and h is the transformation model vector of the source at each sensor. The beamformer procedure aims to create a number of spatial filters w such that $$w^T*X=\hat{s}$$

Where ŝ is the estimate of the source. The formula can be rewritten as $$w^T*h*s=\hat{s}$$

Given the constraints of unity gain to the desired source while attenuating all interfering sources, $$w^T*h=1 \text{ while } w^T*h_{non\ desired\ source}=0$$

The beamformer algorithm seeks to minimise the variance of the filter output in the form of $$w^T=[h^T*\text{Cov}(X)^{-1}*h]^{-1}*h^T*\text{Cov}(X)^{-1}$$

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCES

[Brandstein & Ward; 2001]
EP2997893A1 (OTICON) 23.03.2016
[Manabe & Fukamoto; 2010] H. Manabe, M. Fukamoto, "Using earphones to Perform Gaze Detection for Wearable Interfaces", NTT Docomo Technical Journal, Vol. 12, No. 3, pp. 12-17 (2010).
EP3185590A1 (OTICON) 28.06.2017, co-pending European patent application 16205776.4 (published on 28 Jun. 2017 as EP3185590A1) with the title "A hearing device comprising a sensor for picking up electromagnetic signals from the body", filed at the EPO on 21 Dec. 2016.
[Van Veen & Buckley; 1988] Barry Van Veen & Kevin M. Buckley, Beamforming: A Versatile Approach to Spatial Filtering, IEEE ASSP Magazine, April 1988, pp. 4-24.
[Elliott; 1987]. Douglas F. Elliott, ed., Handbook of Digital Signal Processing: Engineering applications. Academic Press: San Diego, chapter 2, Vaidyanathan, Design and Implementation of Digital FIR Filters]

The invention claimed is:

1. A portable electrooculography (EOG) signal capture system comprising:
   a sensor array adapted for being located at one of a left or right ear of a user, the sensor array comprising a number Ns of electric potential sensors, respectively, for sensing respective electric potentials from the user's head, where Ns is larger than or equal to two; and
   electronic circuitry coupled to the sensor array and configured to provide at least two different combined signals ($S_{BF1}$, $S_{BF2}$), each being representative of a weighted combination of said electric potentials, or of signals derived therefrom, and wherein a difference between said at least two different combined signals ($\Delta P_{BF} = S_{BF1} - S_{BF2}$) represents an electrooculography signal ($\Delta P_{EOG}$) from one or both eyes of said user, said electrooculography signal ($\Delta P_{EOG}$) representing a current eye gaze used to estimate a current eye gaze angle $\Delta\theta$ of the user,
   wherein said combined signals ($S_{BF1}$, $S_{BF2}$) are determined from said electric potentials from the user's head by applying beamformer weights representative of first and second beam patterns (BP1, BP2), respectively, which implement beam patterns that do not attenuate signals from respective first and second target directions of an eye ball of the user,
   wherein functionality of the portable EOG signal capture system is controlled via the current eye gaze angle $\Delta\theta$.

2. A portable electrooculography signal capture system according to claim 1 wherein said electronic circuitry receives a reference potential from a reference sensor.

3. A portable electrooculography signal capture system according to claim 2 comprising respective differential buffers to provide respective voltage difference signals from said electric potentials and said reference potential.

4. A portable electrooculography signal capture system according to claim 3 wherein said electronic circuitry is coupled to the sensor array via said differential buffers to thereby provide that said at least two different combined signals ($S_{BF1}$, $S_{BF2}$) are formed as a weighted combination of said voltage difference signals.

5. A portable electrooculography signal capture system according to claim 1 wherein said beamformed signals ($S_{BF1}$, $S_{BF2}$) are formed by respective fixed beamformers.

6. A portable electrooculography signal capture system according to claim 1 comprising a processor for executing an algorithm, or accessing stored data, providing corresponding values of eye gaze angle and said electrooculography signal ($\Delta P_{EOG}$).

7. A portable electrooculography signal capture system according to claim 1 wherein the electric circuitry is configured to provide that two or more beamformers are adaptive and configured to maximize a difference between the combined signals.

8. A portable electrooculography signal capture system according to claim 1 wherein the electric circuitry is configured to scan a certain part of a skull of the user by adjusting delays and weights used to provide the combined signals.

9. A hearing device adapted for being located at or in an ear of a user, and comprising a portable electrooculography signal capture system according to claim 1.

10. A hearing device according to claim 9 comprising a forward audio signal path comprising an input unit for providing an electric input signal representative of sound, a configurable signal processor for executing a number of processing algorithms to provide a processed electric signal based on said electric input signal, and an output unit for providing stimuli perceivable as sound based on said processed electric signal, wherein said configurable signal processor is adapted to control one or more of said processing algorithms in dependence of said electrooculography signal.

11. A hearing device according to claim 10 wherein said configurable signal processor is adapted to control one or more of said processing algorithms in dependence of said electrooculography signal as well as a brain wave or EEG signals.

12. A hearing device according to claim 11 comprising a number of detectors configured to provide status signals relating to a current physical environment of the hearing device, and/or to a current state of the user wearing the hearing device, and/or to a current state or mode of operation of the hearing device, and wherein said configurable signal processor is adapted to control one or more of said processing algorithms in dependence of said electrooculography signal as well as said status signals.

13. A hearing device according to claim 9 comprising:
an in-the-ear (ITE) part adapted for being located at or in an ear canal of the user wherein said ITE part comprises at least a part of said portable electrooculography signal capture system, and/or
a behind-the-ear (BTE) part adapted for being located at or behind an ear of the user wherein said BTE part comprises at least a part of said electrooculography signal capture system.

14. A hearing device according to claim 9 additionally comprising one or more sensors for picking up potentials from a brain of the user.

15. A hearing device according to claim 9 comprising a hearing aid, a headset, an earphone, an ear protection device or a combination thereof.

16. A hearing system comprising left and right hearing devices according to claim 9.

17. A non-transitory computer readable medium storing an application comprising executable instructions configured to be executed on an auxiliary device to implement a user interface for a hearing device according to claim 9 and wherein the user interface is configured to allow a user to select functions of the hearing device for eye gaze control.

18. A non-transitory computer readable medium according to claim 17 wherein said functions include one or more of selecting a 'Beamforming' mode of operation, controlling 'Volume' and selecting an 'Active wireless receiver'.

19. A non-transitory computer readable medium according to claim 18 configured to provide that 'Beamforming' is controlled by horizontal eye gaze, and 'Volume' is controlled by vertical eye gaze.

20. A portable electrooculography (EOG) signal capture system comprising:
a sensor array adapted for being located at one of a left or right ear of a user, the sensor array comprising a number Ns of electric potential sensors, respectively, for sensing respective electric potentials from the user's head, where Ns is larger than or equal to two; and
electronic circuitry coupled to the sensor array and configured to provide at least two different combined signals ($S_{BF1}$, $S_{BF2}$), each being representative of a weighted combination of said electric potentials, or of voltage difference signals, and wherein a difference between said at least two different combined signals ($\Delta PBF=S_{BF1}-S_{BF2}$) represents an electrooculography signal ($\Delta P_{EOG}$) from one or both eyes of said user, said electrooculography signal ($\Delta P_{EOG}$) representing a current eye gaze used to estimate a current eye gaze angle $\Delta\theta$ of the user,
wherein said electronic circuitry receives a reference potential from a reference sensor, and
said portable electrooculography (EOG) signal capture system comprises respective differential buffers to provide respective voltage difference signals from said electric potentials and said reference potential,
wherein functionality of the portable EOG signal capture system is controlled via the current eye gaze angle $\Delta\theta$.

21. A non-transitory computer readable medium storing an application comprising executable instructions configured to be executed on an auxiliary device to implement a user interface for a hearing device adapted for being located at or in an ear of a user, said hearing device comprising a portable electrooculography signal capture system comprising:
a sensor array adapted for being located at one of a left or right ear, the sensor array comprising a number Ns of electric potential sensors, respectively, for sensing respective electric potentials from the user's head, where Ns is larger than or equal to two; and
electronic circuitry coupled to the sensor array and configured to provide at least two different combined signals ($S_{BF1}$, $S_{BF2}$), each being representative of a weighted combination of said electric potentials, or of signals derived therefrom, and wherein a difference between said at least two different combined signals ($\Delta PBF=S_{BF1}-S_{BF2}$) represents an electrooculography signal ($\Delta P_{EOG}$) from one or both eyes of said user, said electrooculography signal ($\Delta P_{EOG}$) representing a current eye gaze used to estimate a current eye gaze angle $\Delta\theta$ of the user,
wherein said combined signals ($S_{BF1}$, $S_{BF2}$) are determined from said electric potentials from the user's head by applying beamformer weights representative of first and second beam patterns (BP1, BP2), respectively, which implement beam patterns that do not attenuate signals from respective first and second target directions of an eye ball of the user, wherein
the user interface is configured to allow a user to select functions of the hearing device for eye gaze control,
said functions include one or more of selecting a 'Beamforming' mode of operation, controlling 'Volume' and selecting an 'Active wireless receiver,' and
'Beamforming' is controlled by horizontal eye gaze, and 'Volume' is controlled by vertical eye gaze.

* * * * *